(12) United States Patent
McKeon et al.

(10) Patent No.: US 11,524,823 B2
(45) Date of Patent: Dec. 13, 2022

(54) CASE FOR A VAPOR PROVISION DEVICE

(71) Applicant: NICOVENTURES HOLDINGS LIMITED, London (GB)

(72) Inventors: Thomas Michael McKeon, Wheaton, IL (US); Steven Michael Schennum, Plainfield, IL (US)

(73) Assignee: Nicoventures Trading Limited, London (GB)

( * ) Notice: Subject to any disclaimer, the term of this patent is extended or adjusted under 35 U.S.C. 154(b) by 88 days.

(21) Appl. No.: 16/319,389

(22) PCT Filed: Jul. 6, 2017

(86) PCT No.: PCT/GB2017/051992
§ 371 (c)(1),
(2) Date: Jan. 21, 2019

(87) PCT Pub. No.: WO2018/015712
PCT Pub. Date: Jan. 25, 2018

(65) Prior Publication Data
US 2019/0276204 A1 Sep. 12, 2019

Related U.S. Application Data

(60) Provisional application No. 62/365,679, filed on Jul. 22, 2016.

(51) Int. Cl.
*B65D 50/04* (2006.01)
*A61M 15/00* (2006.01)
(Continued)

(52) U.S. Cl.
CPC ............ *B65D 50/046* (2013.01); *A24F 15/01* (2020.01); *A61M 15/0025* (2014.02); *F17C 9/02* (2013.01); *B65D 2215/02* (2013.01)

(58) Field of Classification Search
CPC ...... B65D 50/046; B65D 50/04; B65D 50/02; B65D 50/045; B65D 50/066;
(Continued)

(56) References Cited

U.S. PATENT DOCUMENTS 2,191,016 A * 2/1940 Hoffman ........... A61M 15/0025
128/203.23
3,709,235 A * 1/1973 Washburn .............. A45D 34/00
132/290
(Continued)

FOREIGN PATENT DOCUMENTS

AT 508244 A4 12/2010
CA 2505366 A1 10/2006
(Continued)

OTHER PUBLICATIONS

Application and Filing Receipt for Design U.S. Appl. No. 29/573,612, filed Aug. 8, 2016, Inventors: Nettenstrom et al., 36 pages.
(Continued)

*Primary Examiner* — Robert Poon
(74) *Attorney, Agent, or Firm* — Patterson Thuente, P.A.

(57) ABSTRACT

A case for a cartridge for a vapor provision device is configured such that opening the case involves a coordinated action using both hands. In some implementations, the case includes a first housing portion and a second housing portion which come together to contain and enclose the cartridge when the case is shut and separate to open the case to allow access to the cartridge.

13 Claims, 8 Drawing Sheets

(51) Int. Cl.
*F17C 9/02* (2006.01)
*A24F 15/01* (2020.01)

(58) Field of Classification Search
CPC .......... B65D 2215/02; A61M 15/0025; A24F
15/12; A24F 40/42; A24F 15/00; A24F
15/015; A24F 15/01; A24F 40/40
USPC .......... 206/242, 236; 220/23.87, 23.89, 4.06,
220/4.07, 4.21, 23.86
See application file for complete search history.

(56) References Cited

U.S. PATENT DOCUMENTS

| | | |
|---|---|---|
| D250,485 S | 12/1978 | Cuthbertson |
| D367,526 S | 2/1996 | Bignon |
| 5,564,442 A | 10/1996 | MacDonald et al. |
| D430,358 S | 8/2000 | Papiernik |
| D447,276 S | 8/2001 | Gustafson |
| 6,418,926 B1 | 7/2002 | Chawla |
| D466,644 S | 12/2002 | Cohen Harel |
| D469,962 S | 2/2003 | Campbell et al. |
| D503,996 S | 4/2005 | Mabbutt |
| D504,947 S | 5/2005 | McAuley et al. |
| D505,514 S | 5/2005 | Liu |
| D514,222 S | 1/2006 | Anderson et al. |
| D518,171 S | 3/2006 | Anderson et al. |
| D560,793 S | 1/2008 | Pearl et al. |
| D569,967 S | 5/2008 | Pearl et al. |
| D572,406 S | 7/2008 | Masoud |
| D577,815 S | 9/2008 | Gokhale et al. |
| D579,544 S | 10/2008 | Birath et al. |
| D579,545 S | 10/2008 | Birath et al. |
| D579,546 S | 10/2008 | Birath et al. |
| D579,547 S | 10/2008 | Birath et al. |
| D579,548 S | 10/2008 | Birath et al. |
| D579,549 S | 10/2008 | Birath et al. |
| D579,550 S | 10/2008 | Birath et al. |
| D581,520 S | 11/2008 | Williams et al. |
| D583,463 S | 12/2008 | Wood et al. |
| D590,495 S | 4/2009 | Lulla et al. |
| D590,938 S | 4/2009 | Lulla et al. |
| D591,856 S | 5/2009 | Lulla et al. |
| D613,848 S | 4/2010 | Harvey et al. |
| D614,285 S | 4/2010 | Birath et al. |
| D629,886 S | 12/2010 | Adamo et al. |
| D637,280 S | 5/2011 | Harvey et al. |
| D637,281 S | 5/2011 | Harvey et al. |
| D637,282 S | 5/2011 | Harvey et al. |
| D639,414 S | 6/2011 | Berndt |
| D641,076 S | 7/2011 | Grunstad et al. |
| D646,780 S | 10/2011 | Lulla et al. |
| 8,087,528 B1 * | 1/2012 | Scarlett .............. A47G 23/0216 220/23.89 |
| D659,236 S | 5/2012 | Bobjer et al. |
| D670,374 S | 11/2012 | Bobjer et al. |
| D671,207 S | 11/2012 | Bobjer et al. |
| D684,254 S | 6/2013 | Zuyderhoudt |
| D684,684 S | 6/2013 | Grunstad et al. |
| D692,997 S | 11/2013 | Lovell et al. |
| D693,963 S | 11/2013 | Akopyan |
| D700,227 S | 2/2014 | Kile |
| D700,738 S | 3/2014 | Rennick et al. |
| D710,002 S | 7/2014 | Valentine et al. |
| 8,783,490 B2 * | 7/2014 | Gupta ................... A47J 36/027 220/23.87 |
| D711,528 S | 8/2014 | Grunstad et al. |
| D717,425 S | 11/2014 | Von Schuckmann |
| D726,364 S | 4/2015 | Weigensberg |
| D726,955 S | 4/2015 | Martin |
| D737,419 S | 8/2015 | Emarlou |
| D737,426 S | 8/2015 | Nakamura |
| D745,139 S | 12/2015 | Chen et al. |
| D745,660 S | 12/2015 | Gruntad et al. |
| D761,488 S | 7/2016 | Alarcon et al. |
| D769,438 S | 10/2016 | Crosby et al. |
| D770,088 S | 10/2016 | Abadi et al. |
| D782,109 S | 3/2017 | King |
| D790,123 S | 6/2017 | Beer et al. |
| D790,125 S | 6/2017 | Beer et al. |
| D790,767 S | 6/2017 | Rush et al. |
| D799,750 S | 10/2017 | Parcevaux |
| D820,514 S | 6/2018 | Durand |
| D820,515 S | 6/2018 | Nettenstrom et al. |
| D822,193 S | 7/2018 | Nitta |
| 2002/0040713 A1 | 4/2002 | Eisele et al. |
| 2003/0178024 A1 | 9/2003 | Allan et al. |
| 2003/0235538 A1 | 12/2003 | Zierenberg |
| 2004/0025865 A1 | 2/2004 | Nichols et al. |
| 2004/0025877 A1 | 2/2004 | Crowder et al. |
| 2004/0149283 A1 | 8/2004 | Hochrainer |
| 2005/0005934 A1 | 1/2005 | Harvey |
| 2005/0006273 A1 | 1/2005 | Chawla |
| 2005/0017017 A1 | 1/2005 | Crosby et al. |
| 2005/0022812 A1 | 2/2005 | Hrkach |
| 2005/0103336 A1 | 5/2005 | Nishibayashi et al. |
| 2005/0103337 A1 | 5/2005 | Hickey et al. |
| 2005/0115562 A1 | 6/2005 | Chawla |
| 2005/0205685 A1 | 9/2005 | Jones |
| 2005/0252511 A1 | 11/2005 | Pentafragas |
| 2005/0279357 A1 | 12/2005 | Wachtel |
| 2006/0102175 A1 | 5/2006 | Nelson |
| 2006/0157053 A1 | 7/2006 | Barney et al. |
| 2006/0157054 A1 | 7/2006 | Kuehn et al. |
| 2006/0163269 A1 | 7/2006 | Anderson et al. |
| 2006/0237010 A1 | 10/2006 | De Boer et al. |
| 2006/0237016 A1 | 10/2006 | Wachtel |
| 2007/0045288 A1 | 3/2007 | Nelson |
| 2007/0052544 A1 | 3/2007 | Lintell |
| 2007/0114305 A1 | 5/2007 | Yamaguchi et al. |
| 2007/0125765 A1 | 6/2007 | Nelson |
| 2007/0131805 A1 | 6/2007 | Yamaguchi et al. |
| 2007/0137645 A1 | 6/2007 | Eason et al. |
| 2007/0152086 A1 | 7/2007 | Yamaguchi et al. |
| 2007/0181123 A1 | 8/2007 | Houzego |
| 2007/0215149 A1 | 9/2007 | King et al. |
| 2008/0099015 A1 | 5/2008 | Pocock et al. |
| 2008/0116220 A1 | 5/2008 | Pocock et al. |
| 2008/0196718 A1 | 8/2008 | Connell et al. |
| 2008/0295832 A1 | 12/2008 | Geser et al. |
| 2008/0295834 A1 | 12/2008 | Thoemmes et al. |
| 2008/0314384 A1 | 12/2008 | Harris et al. |
| 2009/0084379 A1 | 4/2009 | Goeckner et al. |
| 2009/0165791 A1 | 7/2009 | Wendland |
| 2009/0183744 A1 | 7/2009 | Hayton et al. |
| 2009/0194105 A1 | 8/2009 | Besseler et al. |
| 2009/0205656 A1 | 8/2009 | Nishibayashi et al. |
| 2009/0250056 A1 | 10/2009 | Pentafragas |
| 2009/0277446 A1 | 11/2009 | Walz |
| 2009/0283095 A1 | 11/2009 | Pocock et al. |
| 2009/0293888 A1 | 12/2009 | Williams et al. |
| 2009/0293892 A1 | 12/2009 | Williams et al. |
| 2009/0314291 A1 | 12/2009 | Anderson et al. |
| 2010/0024812 A1 | 2/2010 | Sugita et al. |
| 2010/0024814 A1 | 2/2010 | Sugita et al. |
| 2010/0059050 A1 | 3/2010 | Wachtel |
| 2010/0059052 A1 | 3/2010 | Davies et al. |
| 2010/0083962 A1 | 4/2010 | Von Schuckmann |
| 2010/0154795 A1 | 6/2010 | Pentafragas |
| 2010/0163042 A1 | 7/2010 | Bhowmick et al. |
| 2010/0189780 A1 | 7/2010 | Walz et al. |
| 2010/0192949 A1 | 8/2010 | Wright et al. |
| 2010/0242960 A1 | 9/2010 | Zangerle |
| 2010/0258120 A1 | 10/2010 | Colomb |
| 2010/0294278 A1 | 11/2010 | Mosier et al. |
| 2011/0000814 A1 * | 1/2011 | Lee ........................ B65D 83/04 206/528 |
| 2011/0041841 A1 | 2/2011 | Wachtel et al. |
| 2011/0067696 A1 | 3/2011 | Sato et al. |
| 2011/0094523 A1 | 4/2011 | Thorens et al. |
| 2011/0120463 A1 | 5/2011 | Esteve et al. |
| 2011/0120465 A1 | 5/2011 | Haerder et al. |
| 2011/0162642 A1 | 7/2011 | Akouka et al. |
| 2011/0174305 A1 | 7/2011 | Bunch et al. |
| 2011/0203586 A1 | 8/2011 | Egen et al. |

(56) References Cited

U.S. PATENT DOCUMENTS

| | | |
|---|---|---|
| 2011/0226236 A1 | 9/2011 | Buchberger |
| 2011/0232637 A1 | 9/2011 | Kaemper et al. |
| 2011/0271958 A1 | 11/2011 | Sawant |
| 2011/0277757 A1 | 11/2011 | Terry et al. |
| 2011/0277760 A1 | 11/2011 | Terry et al. |
| 2012/0037157 A1 | 2/2012 | Rohrschneider et al. |
| 2012/0037158 A1 | 2/2012 | Wachtel et al. |
| 2012/0132205 A1 | 5/2012 | Meliniotis et al. |
| 2012/0247463 A1 | 10/2012 | Zoltan |
| 2012/0260917 A1 | 10/2012 | Bilgic |
| 2013/0047985 A1 | 2/2013 | Harris et al. |
| 2013/0068239 A1 | 3/2013 | Youn |
| 2013/0139815 A1 | 6/2013 | Colomb et al. |
| 2013/0152927 A1 | 6/2013 | Baillet et al. |
| 2013/0152928 A1 | 6/2013 | Kirniak |
| 2013/0174842 A1 | 7/2013 | Young et al. |
| 2013/0186398 A1 | 7/2013 | Baillet et al. |
| 2013/0192615 A1 | 8/2013 | Tucker et al. |
| 2013/0228191 A1 | 9/2013 | Newton |
| 2013/0233313 A1 | 9/2013 | Young et al. |
| 2013/0255679 A1 | 10/2013 | Andrade et al. |
| 2013/0256163 A1* | 10/2013 | Cottle .......... B65D 50/04 206/265 |
| 2013/0269695 A1 | 10/2013 | Brouet et al. |
| 2013/0306065 A1 | 11/2013 | Thorens et al. |
| 2014/0000601 A1 | 1/2014 | Arvidsson et al. |
| 2014/0007875 A1 | 1/2014 | Berg et al. |
| 2014/0076315 A1 | 3/2014 | Von Schuckmann |
| 2014/0083422 A1 | 3/2014 | Arvidsson et al. |
| 2014/0109921 A1 | 4/2014 | Chen |
| 2014/0123989 A1 | 5/2014 | LaMothe |
| 2014/0196717 A1 | 7/2014 | Liu |
| 2014/0238422 A1 | 8/2014 | Plunkett et al. |
| 2014/0238424 A1 | 8/2014 | Macko et al. |
| 2014/0290653 A1 | 10/2014 | Colomb |
| 2014/0318538 A1 | 10/2014 | Bilgic |
| 2014/0360514 A1 | 12/2014 | Zhu |
| 2014/0376895 A1 | 12/2014 | Han |
| 2015/0027457 A1 | 1/2015 | Janardhan et al. |
| 2015/0059747 A1 | 3/2015 | Von Schuckmann |
| 2015/0080808 A1 | 3/2015 | Esteve et al. |
| 2015/0083129 A1 | 3/2015 | Colomb et al. |
| 2015/0096563 A1 | 4/2015 | Toksoz et al. |
| 2015/0107590 A1 | 4/2015 | Colomb |
| 2015/0114391 A1 | 4/2015 | Colomb et al. |
| 2015/0114393 A1 | 4/2015 | Von Schuckmann |
| 2015/0128938 A1 | 5/2015 | Colomb et al. |
| 2015/0128977 A1 | 5/2015 | Li et al. |
| 2015/0144147 A1 | 5/2015 | Li et al. |
| 2015/0164142 A1 | 6/2015 | Li et al. |
| 2015/0174346 A1 | 6/2015 | Dhuppad et al. |
| 2015/0208730 A1 | 7/2015 | Li et al. |
| 2015/0245654 A1 | 9/2015 | Memari et al. |
| 2015/0297841 A1 | 10/2015 | Ono |
| 2015/0298893 A1 | 10/2015 | Welp |
| 2015/0320116 A1 | 11/2015 | Bleloch et al. |
| 2015/0335075 A1 | 11/2015 | Minskoff et al. |
| 2015/0342256 A1 | 12/2015 | Chen |
| 2015/0343159 A1 | 12/2015 | Farr et al. |
| 2016/0001018 A1 | 1/2016 | Fink et al. |
| 2016/0001019 A1 | 1/2016 | Fink et al. |
| 2016/0007654 A1 | 1/2016 | Zhu |
| 2016/0015082 A1 | 1/2016 | Liu |
| 2016/0015912 A1 | 1/2016 | De Kruijf et al. |
| 2016/0022931 A1 | 1/2016 | Althorpe et al. |
| 2016/0045684 A1 | 2/2016 | Ono |
| 2016/0050975 A1 | 2/2016 | Worm et al. |
| 2016/0128386 A1 | 5/2016 | Chen |
| 2016/0143365 A1 | 5/2016 | Liu |
| 2016/0151589 A1 | 6/2016 | Ohrt et al. |
| 2016/0158470 A1 | 6/2016 | Esteve et al. |
| 2016/0175547 A1 | 6/2016 | Nakamura |
| 2016/0219936 A1 | 8/2016 | Alarcon |
| 2016/0264290 A1 | 9/2016 | Hafer et al. |
| 2016/0287818 A1 | 10/2016 | Colomb et al. |
| 2016/0338411 A1 | 11/2016 | Liu |
| 2016/0346488 A1 | 12/2016 | Beller |
| 2016/0367767 A1 | 12/2016 | Cashman et al. |
| 2016/0375207 A1 | 12/2016 | Bhide et al. |
| 2017/0027226 A1* | 2/2017 | Mironov .......... A61M 15/06 |
| 2017/0056608 A1 | 3/2017 | McDerment et al. |
| 2017/0064999 A1 | 3/2017 | Perez et al. |
| 2017/0119057 A1 | 5/2017 | Liu |
| 2017/0127728 A1 | 5/2017 | Li et al. |
| 2017/0208866 A1 | 7/2017 | Liu |
| 2017/0233114 A1* | 8/2017 | Christensen .......... B65B 3/14 141/2 |
| 2017/0325504 A1 | 11/2017 | Liu |
| 2018/0007960 A1 | 1/2018 | Suzuki et al. |
| 2018/0035718 A1 | 2/2018 | Liu |
| 2019/0046745 A1 | 2/2019 | Nettenstrom et al. |
| 2020/0260785 A1* | 8/2020 | Bowen ............ A24B 15/167 |

FOREIGN PATENT DOCUMENTS

| | | |
|---|---|---|
| CN | 300865525 | 9/2007 |
| CN | 300840847 | 10/2008 |
| CN | 300867097 | 12/2008 |
| CN | 301347038 S | 12/2009 |
| CN | 301433957 S | 6/2010 |
| CN | 302012774 S | 3/2012 |
| CN | 302216014 S | 12/2012 |
| CN | 203327957 U | 12/2013 |
| CN | 302926278 S | 1/2014 |
| CN | 203492795 U | 3/2014 |
| CN | 104544567 A | 4/2015 |
| CN | 104544570 A | 4/2015 |
| CN | 303162040 S | 4/2015 |
| CN | 303192526 S | 4/2015 |
| CN | 204317491 U | 5/2015 |
| CN | 303227659 S | 5/2015 |
| CN | 303417607 | 5/2015 |
| CN | 104720114 A | 6/2015 |
| CN | 303234670 S | 6/2015 |
| CN | 303250845 S | 6/2015 |
| CN | 303442703 S | 6/2015 |
| CN | 303535276 S | 6/2015 |
| CN | 104770882 A | 7/2015 |
| CN | 204426686 U | 7/2015 |
| CN | 204444245 U | 7/2015 |
| CN | 303273075 S | 7/2015 |
| CN | 303279026 S | 7/2015 |
| CN | 303300421 S | 7/2015 |
| CN | 303300422 S | 7/2015 |
| CN | 303322969 S | 8/2015 |
| CN | 303322971 S | 8/2015 |
| CN | 303322985 S | 8/2015 |
| CN | 303341926 S | 8/2015 |
| CN | 303350911 S | 8/2015 |
| CN | 303361183 S | 9/2015 |
| CN | 303380240 S | 9/2015 |
| CN | 303380242 S | 9/2015 |
| CN | 303380243 S | 9/2015 |
| CN | 303380252 S | 9/2015 |
| CN | 204682531 U | 10/2015 |
| CN | 303417611 S | 10/2015 |
| CN | 303470028 S | 11/2015 |
| CN | 105768225 A | 7/2016 |
| DE | 95102980001 | 9/1996 |
| DE | 96072850001 | 4/1997 |
| DE | 96072850002 | 4/1997 |
| DE | 499019970001 | 7/1999 |
| DE | 499019970002 | 7/1999 |
| DE | 400039090001 | 8/2000 |
| DE | 401071010001 | 2/2002 |
| DE | 402003030001 | 8/2002 |
| DE | 402093100001 | 3/2003 |
| DE | 402093100002 | 3/2003 |
| DE | 402093100003 | 3/2003 |
| DE | 402093100004 | 3/2003 |
| DE | 402093100005 | 3/2003 |
| DE | 403019480001 | 7/2003 |
| DE | 202013010929 U1 | 12/2013 |
| DE | 96072850003 | 3/2016 |

(56) References Cited

FOREIGN PATENT DOCUMENTS

| | | |
|---|---|---|
| EM | 0001050440001 | 6/2003 |
| EM | 0001050440002 | 6/2003 |
| EM | 0005457690001 | 6/2006 |
| EM | 0007369620001 | 6/2007 |
| EM | 0007369620002 | 6/2007 |
| EM | 0007369620003 | 6/2007 |
| EM | 0007369620004 | 6/2007 |
| EM | 0007369620005 | 6/2007 |
| EM | 0007369620006 | 6/2007 |
| EM | 0007369620007 | 6/2007 |
| EM | 0007369620008 | 6/2007 |
| EM | 0008611410001 | 1/2008 |
| EM | 0015105870001 | 5/2009 |
| EM | 0015105870002 | 5/2009 |
| EM | 0013233070007 | 4/2012 |
| EM | 0013233070008 | 4/2012 |
| EM | 0013233070009 | 4/2012 |
| EM | 0013233070010 | 4/2012 |
| EM | 0013233070011 | 4/2012 |
| EM | 0013233070012 | 4/2012 |
| EM | 0024296960003 | 3/2014 |
| EM | 0024296960004 | 3/2014 |
| EM | 0014157800001 | 7/2014 |
| EM | 0014157800002 | 7/2014 |
| EM | 0014157800003 | 7/2014 |
| EM | 0014157800004 | 7/2014 |
| EM | 0014157800005 | 7/2014 |
| EM | 0014157800006 | 7/2014 |
| EM | 0014157800007 | 7/2014 |
| EM | 0014157800008 | 7/2014 |
| EM | 0014157800009 | 7/2014 |
| EM | 0026967650003 | 5/2015 |
| EM | 0029228640002 | 12/2015 |
| EP | 2460424 A1 | 6/2012 |
| EP | 1496858 B1 | 8/2013 |
| EP | 2801270 A2 | 11/2014 |
| EP | 2875740 A2 | 5/2015 |
| EP | 3039976 A1 | 7/2016 |
| ES | 1016243 U | 11/1991 |
| FR | 970852009 | 8/1997 |
| FR | 983203001 | 10/1998 |
| FR | 956833001 | 1/1999 |
| FR | 001967001 | 7/2000 |
| FR | 007595001 | 4/2001 |
| FR | 007595002 | 4/2001 |
| FR | 011038001 | 5/2001 |
| FR | 011152001 | 5/2001 |
| FR | 011154001 | 5/2001 |
| FR | 201125490001 | 7/2011 |
| FR | 201127120001 | 7/2011 |
| FR | 201127120002 | 7/2011 |
| FR | 201127120003 | 7/2011 |
| FR | 2962339 A1 | 1/2012 |
| FR | 20124875012 | 8/2013 |
| FR | 3039039 A1 | 1/2017 |
| GB | 2047060 A | 11/1980 |
| GB | 1029228 | 4/1986 |
| GB | 2048538 | 11/1995 |
| GB | 2055446 | 8/1996 |
| GB | 2075058 | 9/1998 |
| GB | 2093858 | 8/2000 |
| GB | 2093859 | 8/2000 |
| GB | 4020185 | 11/2011 |
| GB | 2515562 A | 12/2014 |
| GB | 4041108 | 6/2015 |
| IT | 1993MIO0001280003 | 3/1993 |
| IT | 2000TOO0002350001 | 9/2000 |
| IT | 2000TOO0002350003 | 9/2000 |
| IT | 2000TOO0002350004 | 9/2000 |
| IT | 2000TOO0002350006 | 9/2000 |
| IT | 2002TOO0002140001 | 9/2002 |
| IT | 2002TOO0002140002 | 9/2002 |
| IT | 2002TOO0002140003 | 9/2002 |
| IT | 2002TOO0002140004 | 9/2002 |
| JP | D1575098 S | 3/2017 |
| WO | WO-DM264451 | 6/1993 |
| WO | WO-DM0264451 | 6/1996 |
| WO | WO-9912596 A1 | 3/1999 |
| WO | WO-03095005 A1 | 11/2003 |
| WO | WO-2009092520 A1 | 7/2009 |
| WO | WO-2009092653 A1 | 7/2009 |
| WO | WO-2010114504 A1 | 10/2010 |
| WO | WO-2012004512 A1 | 1/2012 |
| WO | WO-2012004514 A1 | 1/2012 |
| WO | WO-2012004518 A1 | 1/2012 |
| WO | WO-2012040512 A2 | 3/2012 |
| WO | WO-2012047181 A1 | 4/2012 |
| WO | WO-2014066730 A1 | 5/2014 |
| WO | WO-2014135224 A1 | 9/2014 |
| WO | WO-2014204417 A1 | 12/2014 |
| WO | WO-2015006838 A1 | 1/2015 |
| WO | WO-2015111017 A1 | 7/2015 |
| WO | WO-2015112750 A1 | 7/2015 |
| WO | WO-2015113743 A1 | 8/2015 |
| WO | WO-2015166239 A1 | 11/2015 |
| WO | WO-2015173303 A1 | 11/2015 |
| WO | WO-2016014652 A1 | 1/2016 |
| WO | WO-2016079410 A1 | 5/2016 |
| WO | WO-2016107764 A2 | 7/2016 |
| WO | WO-2016107767 A1 | 7/2016 |
| WO | WO-2016118005 A1 | 7/2016 |
| WO | WO-2016122417 A1 | 8/2016 |
| WO | WO-2017013130 A1 | 1/2017 |
| WO | WO-DM094223001 | 1/2017 |
| WO | WO-2017163044 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017206211 A1 | 12/2017 |

OTHER PUBLICATIONS

Application and Filing Receipt for Design U.S. Appl. No. 29/590,640, filed Jan. 12, 2017, Inventors: Nettenstrom et al., 18 pages.
Decision for Korean Application No. 3020160038357_M002 dated Dec. 14, 2016., 3 pages.
Decision dated Mar. 14, 2017 for Ukrainian Application No. S201601341, 7 pages.
Decision to Grant dated Aug. 15, 2017 for Russian Application No. 201650539349, 4 pages.
Decision to Grant dated Aug. 28, 2017 for Russian Application No. 201750018449, 4 pages.
Examination Report for Canadian Application No. 169756, dated Nov. 17, 2016, 1 page.
Formalities Notice No. 1 for Australian Design Application No. AU201614224, dated Aug. 9, 2016., 2 pages.
Formalities Notice No. 1 for Australian Design Application No. 201614225, dated Aug. 9, 2016, 2 pages.
International Preliminary Reporton Patentability for Application No. PCT/GB2017/050781, dated Feb. 27, 2018, 13 pages.
International Preliminary Report on Patentability for Application No. PCT/GB2017/050788, dated Aug. 3, 2018, 14 pages.
International Search Report and Written Opinion for Application No. PCT/GB2017/050781 dated Jun. 14, 2017.
International Search Report and Written Opinion for Application No. PCT/GB2017/050788, dated Jun. 7, 2017, 13 pages.
International Search Report and Written Opinion for Application No. PCT/GB2017/050789, dated Jun. 7, 2017, 9 pages.
International Second Written Opinion for PCT Application No. PCT/GB2017/050788, dated Mar. 7, 2018, 9 pages.
Notice of Allowance for Chinese Application No. 201630632827.4, dated Feb. 24, 2017, 2 pages.
Notice of Allowance for Japanese Application No. 2016016955, dated Feb. 14, 2017, 2 pages.
Notice of Allowance for Japanese Application No. 2016016956, dated Feb. 14, 2017, 2 pages.
Notice of Allowance for Japanese Application No. 2017-000313, dated Dec. 19, 2017, 3 pages.
Notice of Issuance for Chinese Application No. 201630370608.3, dated Dec. 30, 2016, 3 pages.

(56) References Cited

OTHER PUBLICATIONS

Office Action for Chinese Application No. 201630370608.3, dated Nov. 1, 2016, 1 page.
Office Action for Japanese Application No. 2017-000313, dated Aug. 29, 2017, 4 pages.
Office Action dated Feb. 21, 2017 for Russian Application No. 2016505393.
Office Action dated Jan. 13, 2017 for Ukrainian Application No. S201601341, 1 pages.
Office Action dated Nov. 23, 2016 for Mexican Application No. MX/f/2016/002430, 1 pages.
Office Action dated Oct. 6, 2016 for Russian Application No. 2016503052, 2 pages.
Search Report dated Aug. 11, 2016 for Great Britain Application No. 1605104.7, 5 pages.
Search Report dated Aug. 16, 2016 for Great Britain Application No. 1605103.9, 4 pages.
Search Report dated Aug. 25, 2016 for Great Britain Application No. 1605100.5, 3 pages.
Search Report dated Aug. 3, 2016 for Great Britain Application 1605106.2, 5 pages.
Search Report dated Jun. 9, 2017 for Great Britain Application No. 1612684.9, 4 pages.
Electronic Cigarette | Vype Pebble | Govype, post date n/a, (c)n/a, govype.com, Aug. 30, 2017, https://www.govype.com/uk/vype-pebble-starter-kit. 2 pages.
First Office Action dated Oct. 23, 2019 for Chinese Application No. 201780045176,0, 19 pages.
Innokin EQ Pod System Vape Kit by vapeclub. dated 2018. found online [Sep. 24, 2018] https://www.vapeclub.co.uk/pods-and-closed-system-vape-starter-- kits/innokin-eq-pod-system-vape-kit.html, 6 pages.
International Preliminary Report on Patentability for Application No. PCT/GB2017/051992, dated Oct. 22, 2018, 18 pages.
International Search Report and Written Opinion for Application No. PCT/GB2017/051992, dated Nov. 15, 2017, 18 pages.
International Preliminary Report on Patentability for International Application No. PCT/EP2015/055972, dated Jul. 19, 2016, 22 pages.
International Search Report for corresponding Application No. PCT/EP2015/055972 dated Sep. 3, 2015, 4 pages.
JustFog C601 Pod System Vape Kit by vapeclub. dated 2018. https://www.vapeclub.co.uk/pods-and-closed-system-vape-starter-kits/justfog-c601-pod-system-vape-kit.html, 6 pages.
Office Action dated May 22, 2020 for Chinese Application No. 201780045176,0, 18 pages.
Smoant S8 Ultra-Portable System Kit _ Premium Electronic Cigarette by wicked vapor, mailed 2018, found online on Sep. 24, 2018, at https://wicked-vapor.com/products/smoant-s8-ultra-portable-system-kit, 2 pages.
Vincent V., "Renova Vapor Zero vape Pod Kit", posted May 29, 2018, retrieved Sep. 24, 2018, https://www.e-cigarette-forum.com/threads/renova-vapor-zero-vape-pod-kit-hqd-comma-vape-pod-kit-wismec-hiflask-pod-kit.865421/.
Written Opinion for corresponding International Application No. PCT/EP2015/055972, dated Sep. 3, 2015, 6 pages.

* cited by examiner

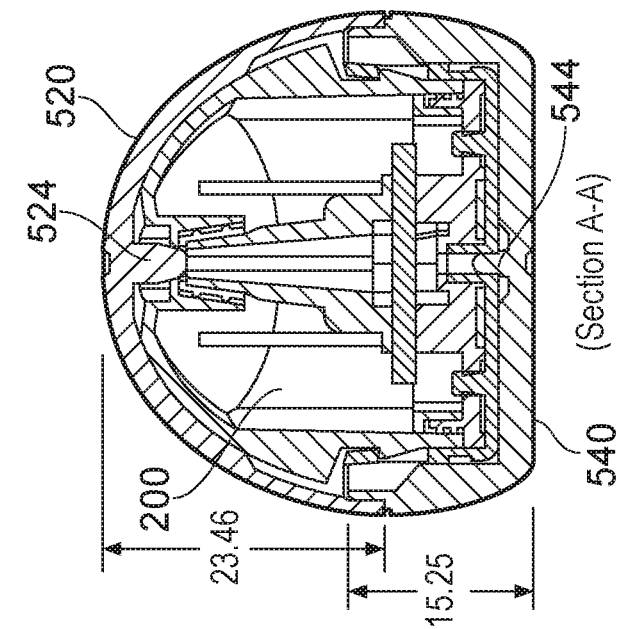
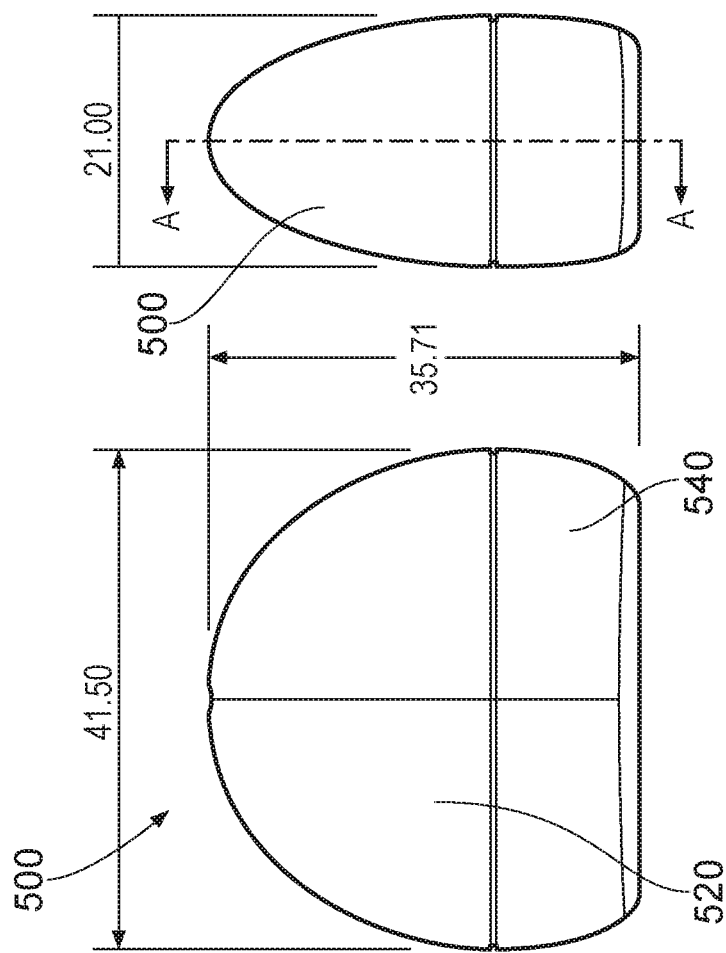
FIG. 6A  FIG. 6B  FIG. 6C

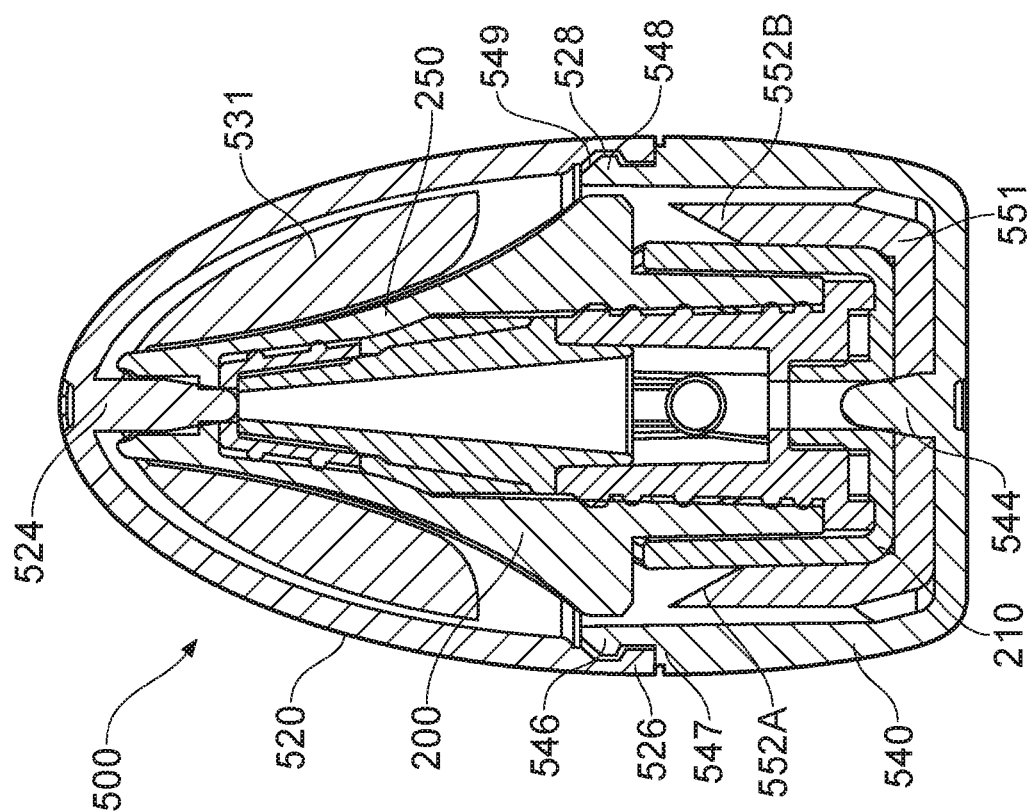
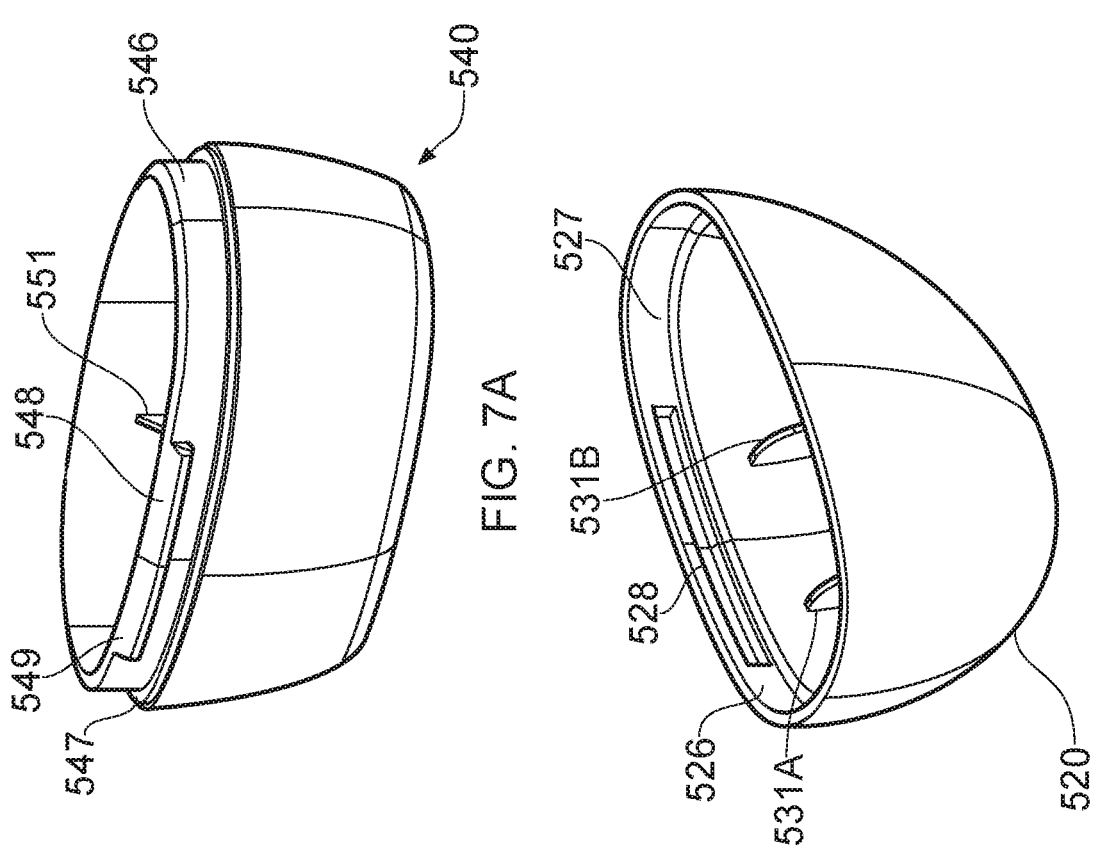

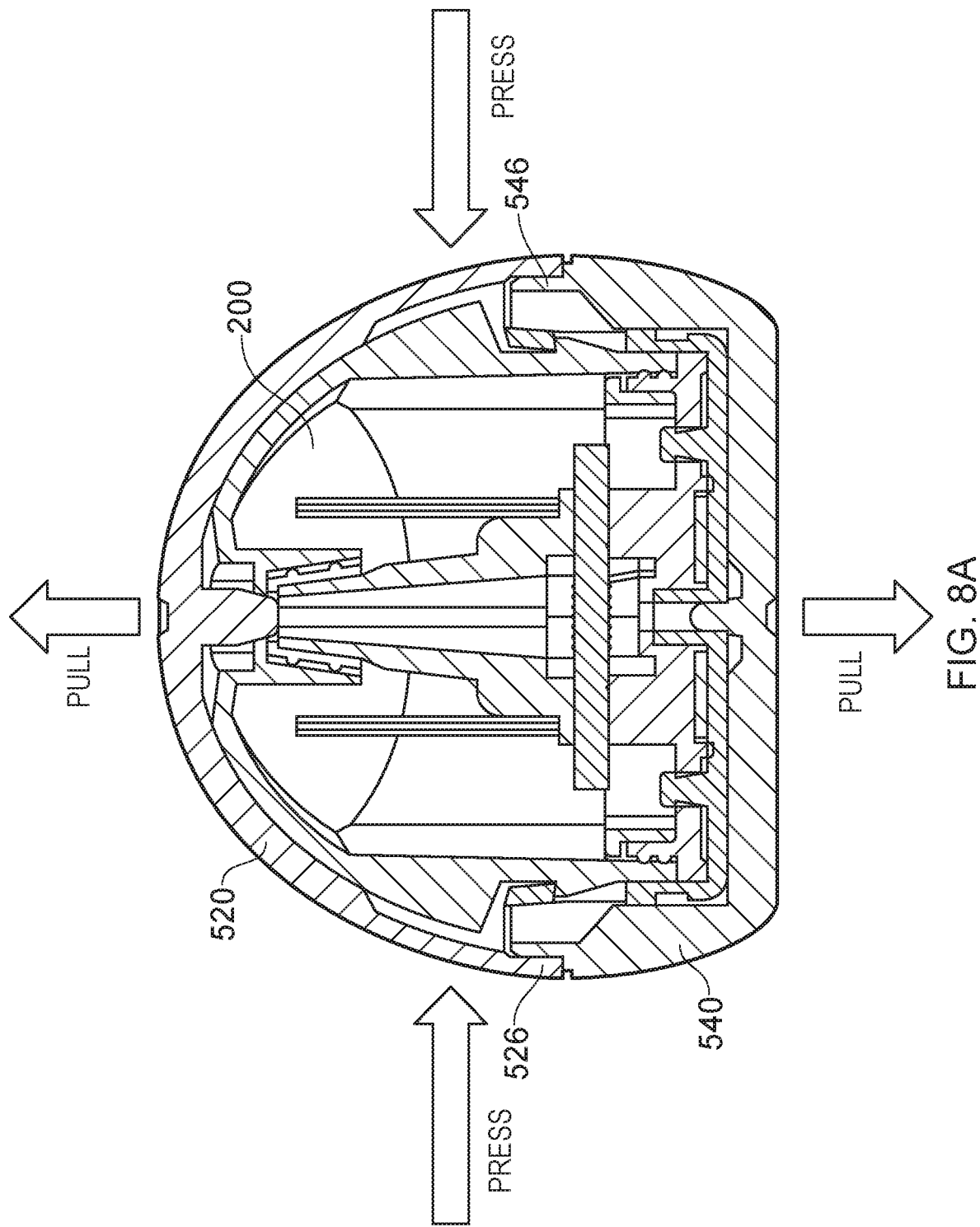

CASE FOR A VAPOR PROVISION DEVICE

PRIORITY CLAIM

The present application is a National Phase entry of PCT Application No. PCT/GB2017/051992, filed Jul. 6, 2017, which claims priority from U.S. Provisional Application No. 62/365,679, filed Jul. 22, 2016, each of which is hereby fully incorporated herein by reference.

TECHNICAL FIELD

The present disclosure relates to a case for a vapor provision device, e.g. an e-cigarette, and other similar devices.

BACKGROUND

Many electronic vapor provision systems, such as e-cigarettes and other electronic nicotine delivery systems, are formed from two main components—a cartomizer and a control unit. The cartomizer generally includes a reservoir of liquid and an atomizer for vaporizing the liquid. The atomizer is often implemented as an electrical (resistive) heater, such as a coil of wire. The control unit generally includes a battery for supplying power to the atomizer. In operation, the control unit may be activated, for example by detecting when a user inhales on the device and/or when the user presses a button, to provide electrical power from the battery to the heater. This activation causes the heater to vaporize a small amount of liquid from the reservoir, which is then inhaled by the user.

This type of e-cigarette therefore generally incorporates two consumables, firstly the liquid to be vaporized, and secondly power in the battery. Regarding the former, once the reservoir of liquid has been exhausted, the cartomizer may be discarded to allow replacement with a new cartomizer. Regarding the latter, the control unit may provide some form of electrical connector for receiving power from an external source, thereby allowing the battery within the e-cigarette to be re-charged.

Although e-cigarettes and their ancillaries have developed rapidly over the past few years, there remain areas where it is desirable to improve the operability and user experience for such devices.

SUMMARY

The disclosure is defined in the appended claims.

Provided herein is a case for a cartridge for a vapor provision device, the case being configured such that opening the case involves a coordinated action using both hands. Also provided herein is a case for a cartridge for a vapor provision device, the case comprising a first housing portion and a second housing portion which separate to open the case to allow access to the cartridge, wherein the case is configured such that the cartridge is held in the first housing portion after the case is opened. Also provided herein is a case for a cartridge for a vapor provision device, the case configured to provide a substantially rigid housing that fits closely around the cartridge when detached from the electronic vapor provision device, the housing when closed providing a sealed environment for the cartridge. It will be appreciated that these different features may all be implemented in the same case.

BRIEF DESCRIPTION OF THE DRAWINGS

Various embodiments of the disclosure will now be described in detail by way of example only with reference to the following drawings:

FIGS. 6A and 6B show a front view and a side view respectively of the case of FIG. 5 in a closed configuration in accordance with some embodiments.

FIG. 6C shows a section through the case of FIGS. 6A and 6B and a cartomizer located inside the case. The section is taken through the center of the case and cartomizer in a plane extending from one side of the case/cartomizer to the opposite side.

FIGS. 7A and 7B show more details of the bottom housing and top housing respectively of the case in accordance with some embodiments.

FIG. 7C shows a section through the case of FIGS. 6A and 6B and a cartomizer located inside the case. The section is taken through the center of the case and cartomizer in a plane extending from the front face to the back face of the case/cartomizer.

FIG. 8A is a section through the case and cartomizer therein corresponding to the section of FIG. 6C, but additionally illustrating a method of opening the case.

DETAILED DESCRIPTION

Figure 1:
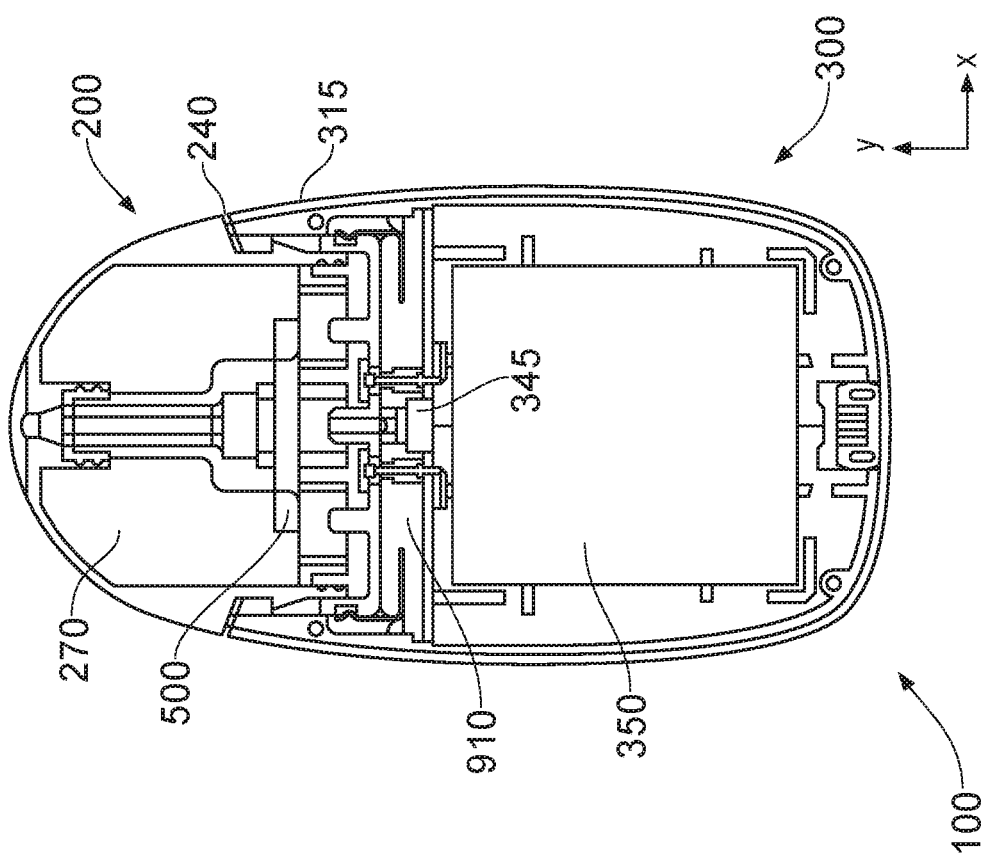
FIG. 1 is a cross-section through an e-cigarette comprising a cartomizer and a control unit.

FIG. 1 is a cross-section through an e-cigarette 100. The e-cigarette 100 comprises two main components, namely a cartomizer 200 and a control unit 300. The cartomizer 200 includes a chamber 270 containing a reservoir of liquid, a heater to act as an atomizer or vaporizer, and a mouthpiece. The liquid in the reservoir (sometimes referred to as the e-liquid) typically includes nicotine in an appropriate solvent, and may include further constituents, for example, to aid aerosol formation, and/or for additional flavoring. The cartomizer 200 further includes a wick/heater assembly 500, which includes a wick or similar facility to transport a small amount of liquid from the reservoir to a heating location on or adjacent the heater. The control unit 300 includes a re-chargeable cell or battery 350 to provide power to the e-cigarette 100, a printed circuit board (PCB) for generally controlling the e-cigarette 100 (not shown in FIG. 1), and a microphone 345 for detecting a user inhalation (via a pressure drop). When the heater receives power from the battery, as controlled by the PCB in response to the microphone 345 detecting a user puff on the e-cigarette 100, the heater vaporizes the liquid from the wick and this vapor is then inhaled by a user through the mouthpiece.

For ease of reference, the x and y axes are marked in FIG. 1. The x axis will be referred to herein as the width of the device (from side to side), while the y axis will be referred to herein as the height axis, where the cartomizer 200 represents the upper portion of the e-cigarette 100 and the control unit 300 represents the lower portion of the e-cigarette 100. Note that this orientation reflects how a user holds the e-cigarette 100 during normal operation of the device, given that the wick is located in the lower part of the reservoir in the cartomizer 200. Therefore holding the e-cigarette 100 in this orientation ensures that the wick is in contact with liquid at the bottom of the reservoir.

We further assume a z axis (not shown in FIG. 1) which is perpendicular to the x and y axes shown in FIG. 1. The z axis will be referred to herein as the depth axis. The depth of e-cigarette 100 is significantly less than the width of the e-cigarette 100, thereby resulting in a generally flat or planar configuration (in the x-y plane). Accordingly, the z axis can be considered as extending from face to face of the e-cigarette 100, where one face may be regarded (arbitrarily) as the front face of the e-cigarette 100 and the opposing face as the back face of the e-cigarette 100.

The cartomizer 200 and the control unit 300 are detachable from one another by separating in a direction parallel to the y-axis, but are joined together when the device 100 is in use so as to provide mechanical and electrical connectivity between the cartomizer 200 and the control unit 300. When the e-liquid in cartomizer reservoir 270 has been depleted, the cartomizer 200 is removed and a new cartomizer is attached to the control unit 300. Accordingly, the cartomizer 200 may sometimes be referred to as the disposable portion of the e-cigarette 100, while the control unit 300 represents the re-usable portion.

Figure 2:
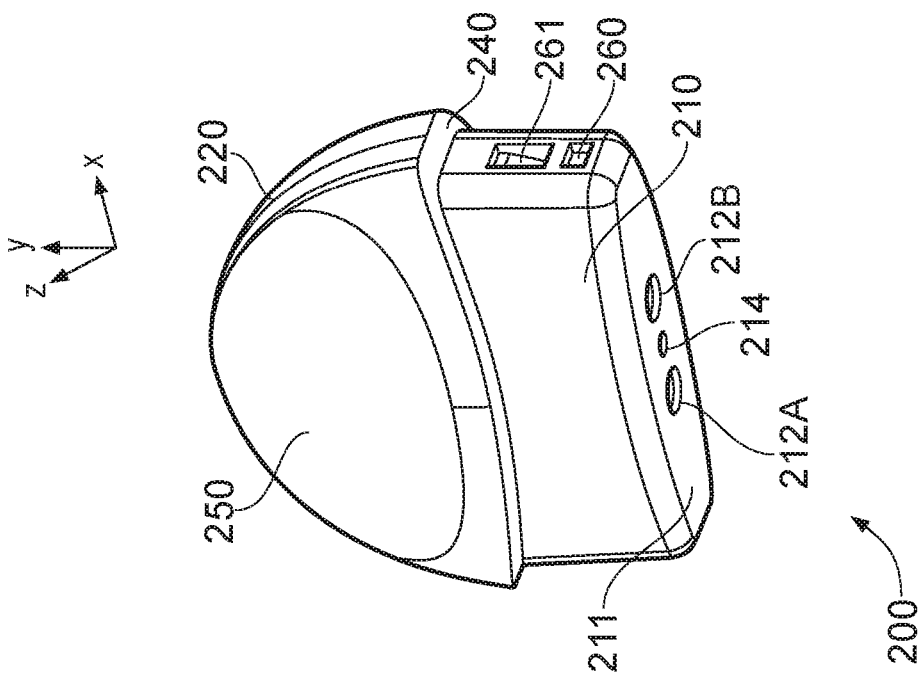
FIG. 2 is an isometric external view of the cartomizer of the e-cigarette of FIG. 1.

FIG. 2 is an isometric external view of the cartomizer 200 of the e-cigarette 100 of FIG. 1. This external view confirms that the depth of the cartomizer 200 (and the e-cigarette 100 as a whole), as measured parallel to the z axis, is significantly less than the width of the cartomizer 200 (and the e-cigarette 100 as a whole), as measured parallel to the x axis. Note that overall, the external appearance of the cartomizer 200 is relatively smooth and uncluttered.

The cartomizer 200 comprises two main portions (at least from an external viewpoint). In particular, there is a lower or base portion 210 and an upper portion 220. The upper portion 220 provides the mouthpiece 250 of the e-cigarette 100, as described in more detail below. When the cartomizer 200 is assembled with the control unit 300, the base portion 210 of the cartomizer 200 sits within the control unit 300, and hence is not externally visible, whereas the upper portion 220 of the cartomizer 200 protrudes above the control unit 300, and hence is externally visible. Accordingly, the depth and width of the base portion 210 are smaller than the depth and width of the upper portion 220, to allow the base portion to fit within the control unit 300. The increase in depth and width of the upper portion 220 compared with the base portion 210 is provided by a lip or rim 240. When the cartomizer 200 is inserted into the control unit 300, this lip or rim 240 abuts against the top of the control unit 300.

As shown in FIG. 2, the side wall of base portion 210 includes a notch or indentation 260 for receiving a corresponding latching member from the control unit 300. The opposite side wall of the base portion 210 is provided with a similar notch or indentation to likewise receive a corresponding latching member from the control unit 300. It will be appreciated that this pair of notches 260 on the base portion 200 (and the corresponding latching members of the control unit 300) provide a latch or snap fit connection for securely retaining the cartomizer 200 within the control unit 300 during operation of the device 100. Adjacent to the notch 260 is a further notch or indentation 261, which is utilized in the formation of the cartomizer 200, as described in more detail below.

As also shown in FIG. 2, the bottom wall 211 of the base portion 210 includes two larger holes 212A, 212B on either side of a smaller hole 214 for air inlet. The larger holes 212A and 212B are used to provide positive and negative electrical connections from the control unit 300 to the cartomizer 200. Thus when a user inhales through the mouthpiece 250 and the device 100 is activated, air flows into the cartomizer 200 through the air inlet hole 214. This incoming air flows past the heater (not visible in FIG. 2), which receives electrical power from the battery in the control unit 300 so as to vaporize liquid from the reservoir (and more especially from the wick). This vaporized liquid is then incorporated or entrained into the airflow through the cartomizer 200, and hence is drawn out of the cartomizer 200 through mouthpiece 250 for inhalation by the user.

Figure 3:
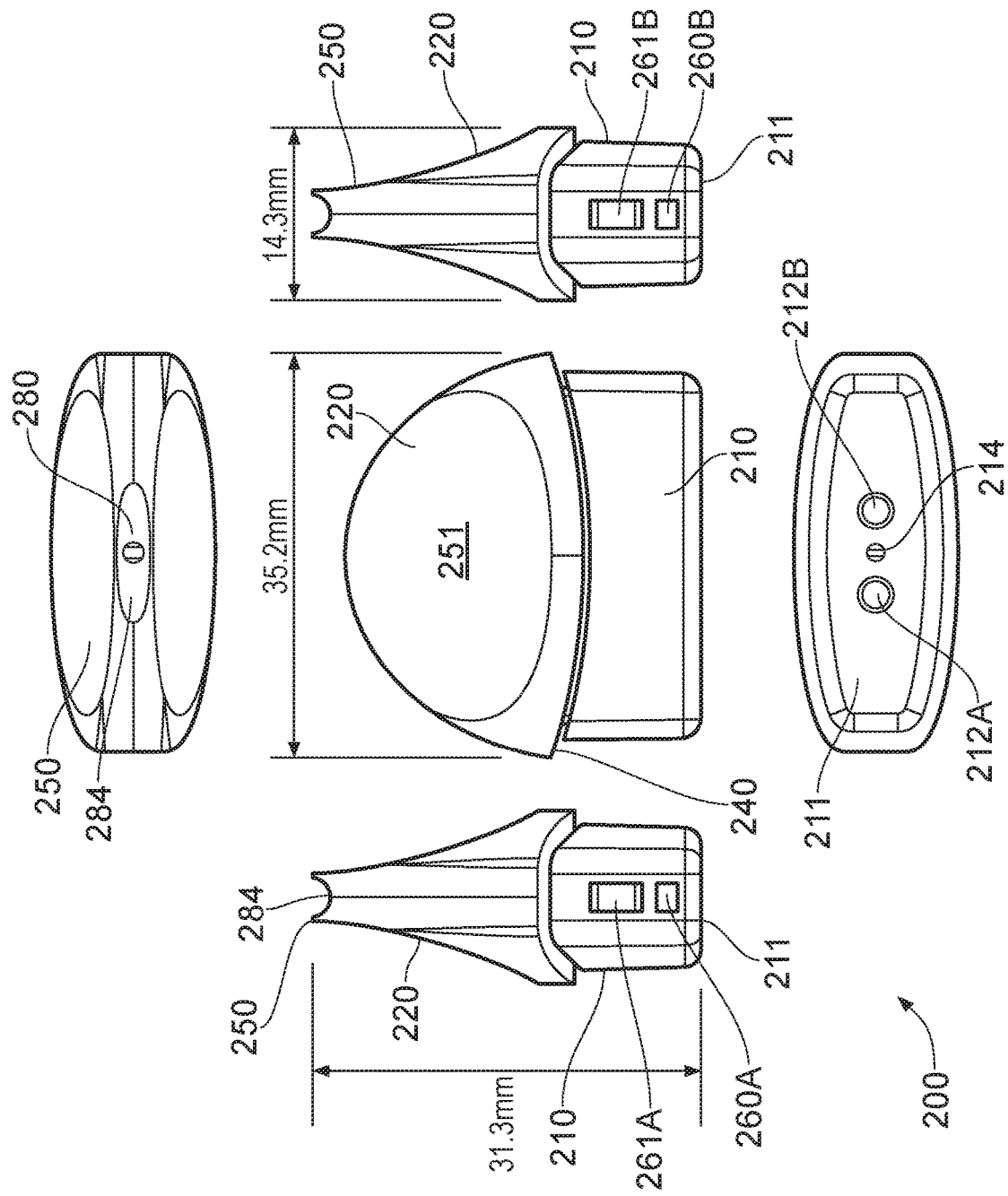
FIG. 3 is a collection of five external views of the cartomizer of FIG. 2. In particular, the bottom view shows the cartomizer from underneath, the top view shows the cartomizer from above, the central view shows a face view of the cartomizer (from front or back), and on either side of the central view are respective side views of the cartomizer.

FIG. 3 is a collection of five external views of the cartomizer 200 of FIG. 2. In particular, the bottom view shows the cartomizer 200 from underneath, the top view shows the cartomizer 200 from above, the central view shows a face view of the cartomizer 200 (from front or back), and on either side of the central view are respective side views of the cartomizer 200. Note that since the cartomizer 200 is symmetric front/back (i.e. with respect to the z axis), the front face of the cartomizer 200 and the back face of the cartomizer 200 both correspond to the central view of FIG. 3. In addition, the cartomizer 200 is also symmetric in the width direction (i.e. with respect to the x axis), hence the two side views to the left and right of the central view are the same.

FIG. 3 illustrates the various features of the cartomizer 200 already discussed above with respect to FIG. 2. For example, the central view clearly shows the top portion 220 and the bottom portion 210 of the cartomizer 200. The lower view shows the bottom wall of the base portion 211, including the two larger holes 212A and 212B, which are used to provide positive and negative electrical connections from the control unit 300 to the cartomizer 200, plus the smaller hole 214 for air inlet into the cartomizer 200. In addition, the two side views show the two notches in each side wall, an upper notch 261A, 261B, and a lower notch 260A, 260B, the latter being used to fasten the cartomizer 200 to the control unit 300.

The top view further shows a hole 280 in the mouthpiece 250 which represents the air outlet from the cartomizer 200. Thus in operation, when a user inhales, air enters the cartomizer 200 at the bottom through inlet 214, flows through the atomizer, including past the heater, where it acquires vapor, and then travels up the center of the cartomizer 200 to exit through air outlet 280.

FIG. 3 provides dimensions of the cartomizer 200, showing a maximum height (in the y direction) of 31.3 mm, a maximum width (in the x direction) of 35.2 mm, and a maximum depth of 14.3 mm (parallel to the z direction). Note that these maximum width and depth measurements relate to the upper portion 220 of the cartomizer 200; the width and depth of the base portion 210 are somewhat smaller, in order to allow the base portion 210 to be received into the control unit 300. The difference in width and depth between the upper portion 220 and the base portion 210 is accommodated by the rim or flange 240, as described above.

It will be appreciated that the dimensions shown in FIG. 3 are provided by way of example only, and may vary between embodiments. Nevertheless, the dimensions given do confirm that the e-cigarette 100, including the cartomizer 200, has an approximately flat or planar shape, with one relatively small dimension (the z direction) perpendicular to the planar shape. This planar shape is extended by the control unit 300, which in effect extends the height (y dimension of the cartomizer 200), but shares substantially the same width and depth.

FIG. 3 also gives a clear indication of the size and shape of the mouthpiece 250. In contrast to many e-cigarettes, which provide a circular mouthpiece akin to a straw or conventional cigarette, the mouthpiece 250 has a very different and distinctive shape. In particular, the mouthpiece 250 comprises a pair of large, relatively flat, opposing faces. One of these mouthpiece faces is denoted as face 251 in the central view of FIG. 3, and there is a corresponding, opposing face to the rear of the device. (Note that the labeling of front and back for the cartomizer 200 is arbitrary, since it is symmetric with respect to the z axis, and can be fitted either way around onto the control unit 300.)

The front and rear faces provide relatively large surfaces onto which the lips of a user can be placed. For example, we can consider the front face to provide a surface for engaging the upper lip, and the rear face to provide a surface for engaging the lower lip. In this configuration, we can regard the height (y axis) of the e-cigarette 100 defining a longitudinal axis extending away from the user's mouth, the width of the e-cigarette 100 (the x axis) as running parallel to the line between a user's upper and lower lips, and the depth of the e-cigarette 100 (the z axis) as running parallel to the direction of separation of the user's upper and lower lips.

The height of the front and rear mouthpiece faces (approximately 17 mm in the particular embodiment of FIG. 3) is broadly comparable to the typical thickness of a lip, and therefore large enough to readily accommodate in this direction a lip placed on the surface. Similarly, the width of the front and rear mouthpiece faces (approximately 28 mm in the particular embodiment of FIG. 3) represents a significant proportion (very approximately half) of the typical width of lips (from one side of the mouth to the other).

This shape and sizing of the mouthpiece 250 allows the lips of user to engage the mouthpiece 250 for inhalation with much less distortion from the normal resting position of the mouth—e.g. there is no need to purse the lips, as for a straw or conventional cigarette having a small circular mouthpiece. This makes using the mouthpiece 250 of the e-cigarette 100 a more relaxing experience, and also may help to ensure a more consistent seal between the mouth and the mouthpiece 250.

In addition, e-cigarette 100 (like many other e-cigarettes) uses a sensor to detect airflow through the device, i.e. a user puff, which can then trigger operation of the heater to vaporize the liquid. The device 100 has to discriminate between the airflow caused by a user puff, and other forms of airflow or pressure changes that arise due to other actions or circumstances—e.g. movement of the e-cigarette 100 through the air, being on a railway train which enters a tunnel, etc. Having a consistent seal between the mouth and the mouthpiece 250 can help the device provide better discrimination of an actual inhalation, and so reduce the risk of unintentional activation of the heater.

Furthermore, some e-cigarettes use sensor measurements of the airflow through the device not only to initiate activation of the heater, but also to provide dynamic control of the heater (or other components of the e-cigarette 100). For example, as the measured airflow increases, the heater may be provided with more power, firstly to compensate for the cooling effect of the increased airflow, and/or secondly to vaporize more liquid into the increased airflow. Having a consistent seal between the mouth and the mouthpiece 250 can again help to improve the reliability and accuracy of this dynamic control.

In addition, with reference to the side views of FIG. 3, it can be seen that the front and back faces of the mouthpiece 250 generally slope towards one another at the top of the device. In other words, the depth or separation of the opposing faces (as measured in the z direction) decreases towards the air outlet hole 280 (i.e. as the y axis increases). This slope is relatively gentle—approximately 15 degrees with respect to the y axis. This incline helps to provide a natural and comfortable engagement between the faces of the mouthpiece 251 and the lips of a user.

As can be seen in FIG. 3, the front and back faces 251 do not converge completely at the top of the mouthpiece 250, but rather overhang to provide a small valley 284 which extends in the x-direction of the device. The opening 280, which allows air and vapor to exit from the cartomizer 200, is formed in the center of this valley 284. Having this small overhang, so that the mouthpiece opening 280 is located in the groove or valley 284, helps to protect the mouthpiece opening from physical contact, and hence from potential damage and dirt.

Figure 4:
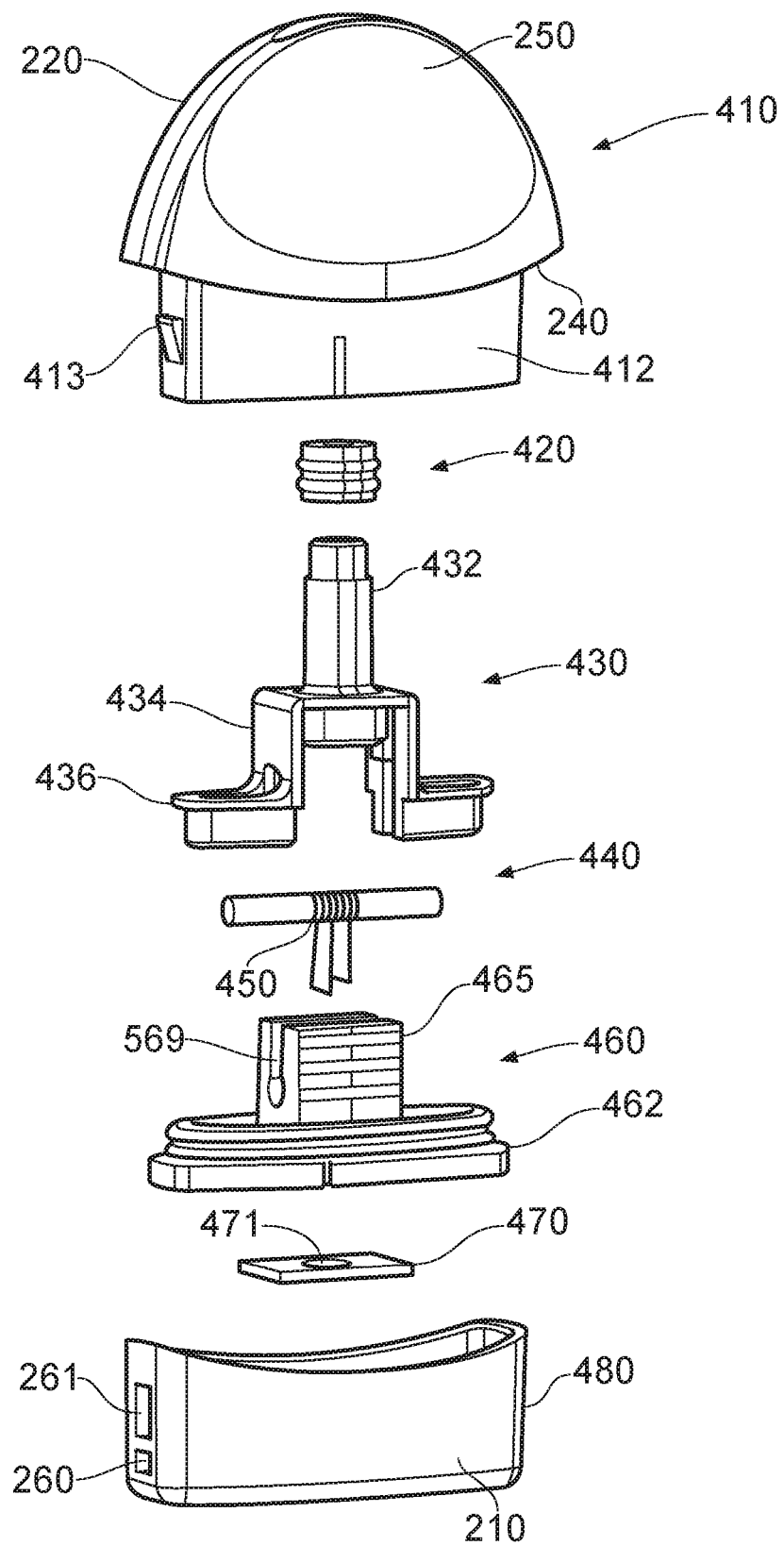
FIG. 4 is an exploded view of the cartomizer of the e-cigarette of FIG. 1.

FIG. 4 is an exploded view of the cartomizer 200 of the e-cigarette 100 of FIG. 1. The cartomizer 200 includes a shell 410, a vent seal 420, an inner frame 430, a heating coil 450 located on a wick 440, a primary seal 460 (also referred to as the cartomizer plug), a printed circuit board (PCB) 470 and an end cap 480. The view of FIG. 4 shows the above components exploded along the longitudinal (height or y) axis of the cartomizer 200.

The cap 480 is formed from substantially rigid plastic such as polypropylene and provides the base portion 210 of the cartomizer 200. The cap 480 is provided with two holes 260, 261 on each side (only one side is visible in FIG. 4, but the side which is not visible is the same as the side that is visible). The lower hole 260 is for latching the cartomizer 200 to the control unit 300, while the upper hole 261 is for latching the end cap 480 to the shell 410. As described in more detail below, latching the cap 480 and the shell 410 in effect completes the assembly of the cartomizer 200, and retains the various components shown in FIG. 4 in the correct position.

Above the end cap is located the PCB 470, which includes a central air hole 471 to allow air to flow through the PCB 470 into the atomizer (the end cap 480 is likewise provided with a central air hole, not visible in FIG. 4) to support this air flow into the atomizer. In accordance with some embodiments, the PCB 470 does not contain any active electrical components, but rather provides a circuit or conductive path between the control unit 300 and the heater 450.

Above the PCB 470 is located the primary seal 460, which has two main portions, an upper portion which defines (in part) an atomizer chamber 465, and a lower portion 462 which acts as an end seal for the reservoir 270. Note that in the assembled cartomizer 200, the reservoir of e-liquid is located around the outside of the atomizer chamber, and the e-liquid is prevented from leaving the cartomizer 200 (at least in part) by the lower portion 462 of the cartomizer plug 460. The cartomizer plug 460 is made from a material that is slightly deformable. This allows the lower portion 462 to be compressed a little when inserted into the shell 410, and hence provide a good seal to retain the e-liquid in reservoir 270.

Two opposing side walls of the atomizer chamber 465 are provided with respective slots 569 into which the wick 440 is inserted. This configuration thereby ensures that the heater 450, which is positioned on the wick, is located near the bottom of the atomizer chamber to vaporize liquid introduced into the atomizer chamber 465 by wick 440. In some embodiments, the wick 440 is made of glass fiber rope (i.e. filaments or strands of glass fiber twisted together), and the heater coil 450 is made of nichrome (an alloy of nickel and chromium). However, various other types of wick and heater are known and could be used in the cartomizer 200, such as a wick made out of porous ceramic, and/or some form of planar heater (rather than a coil). Note that although FIG. 4 suggests that the heater coil 450 has a loop of wire dropping down from the wick at each end, in practice there is just a single lead at each end (as described in more detail below).

The cartomizer plug 460 and the wick/heater assembly are surmounted by the inner frame 430, which has three main sections. The inner frame is substantially rigid, and may be made of a material such as polybutylene terephthalate. The lowermost section 436 of the inner frame 430 covers the lower portion 462 of the cartomizer plug 460, while the middle section 434 completes the atomizer chamber 465 of the cartomizer plug 460. In particular, the inner frame provides the top wall of the atomizer chamber, and also two side walls that overlap with the two side walls of the atomizing chamber 465 of the cartomizer plug 460. The final section of the inner frame is an airflow tube 432 that leads upwards from the top wall of the atomizing chamber (part of the middle section 434) and connects with the mouthpiece hole 280. In other words, tube 432 provides a passage for vapor produced in the atomizing chamber 465 to be drawn out of the e-cigarette 100 and inhaled through mouthpiece 250.

Since the inner frame is substantially rigid, the vent seal 420 is provided at (inserted around) the top of the airflow tube 432 to ensure a proper seal between the inner frame and the mouthpiece exit hole 280. The vent seal 420 is made of a suitably deformable and resilient material such as silicone. Lastly, the shell 410 provides the external surface of the upper portion 220 of the cartomizer 200, including the mouthpiece 250, and also the lip or flange 240. The shell 410, like the end cap, is formed of a substantially rigid material, such as polypropylene. The lower section 412 of the shell 410 (i.e. below the lip 240) sits inside the end cap 480 when the cartomizer 200 has been assembled. The shell is provided with a latch tab 413 on each side to engage with hole 261 on each side of the end cap 480, thereby retaining the cartomizer 200 in its assembled condition.

The airflow passage through the cartomizer 200 enters a central hole in the cap 480 (not visible in FIG. 4) and then passes through a hole 471 in the PCB 470. The airflow next passes up into the atomizer chamber 465, which is formed as part of the cartomizer plug 460, flows around the wick and heater assembly 500 and through the tube 432 of the inner frame 430 (and through vent seal 420), and finally exits through the hole 280 in the mouthpiece 250.

The reservoir 270 of e-liquid is contained in the space between this airflow passage and the outer surface of the cartomizer 200. Thus shell 410 provides the outer walls (and top) of the housing for the reservoir 270, while the lower section 436 of the inner frame in conjunction with the base portion 462 of the primary seal 460 and end cap 480 provide the bottom or floor of the housing for the reservoir of e-liquid. The inner walls of this housing are provided by the atomizing chamber 465 of the primary seal 460, in cooperation with the middle section 434 of the inner frame, and also the airflow tube 432 of the inner frame 430 and the vent seal 420. In other words, the e-liquid is stored in the reservoir space between the outer walls and the inner walls. However, the e-liquid should not penetrate inside the inner walls, into the airflow passage, except via wick 440, otherwise there is a risk that liquid would leak out of the mouthpiece hole 280.

The capacity of this space is typically of the order of 2 ml in accordance with some embodiments, although it will be appreciated that this capacity will vary according to the particular features of any given design. Note that unlike for some e-cigarettes, the e-liquid reservoir 270 is not provided with any absorbent material (such as cotton, sponge, foam, etc) for holding the e-liquid. Rather, the reservoir chamber only contains the liquid, so that the liquid can move freely around the reservoir 270. This has certain advantages, such as generally supporting a larger capacity, and also making the filling procedure less complex. One potential disadvantage with having a free liquid in the reservoir (i.e. not holding the liquid in a sponge or other absorbent structure) is that the liquid can flow more easily, and hence might be more likely to leak in an undesirable manner from the reservoir 270 into the airflow passage. However, such leakage is generally prevented by the vent seal 420 and the primary seal 460.

Figure 5:
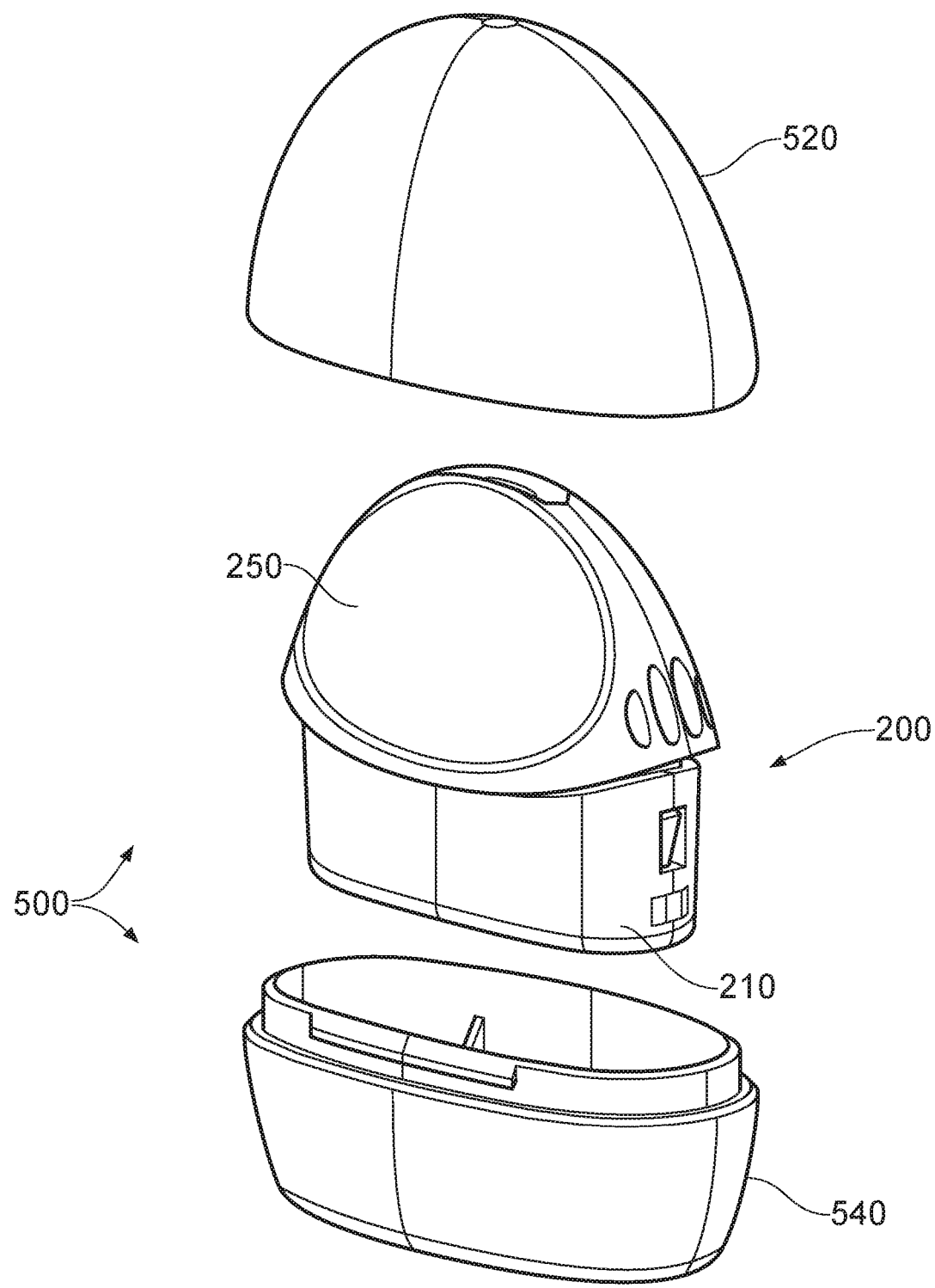
FIG. 5 shows an exploded (open) view of a case in accordance with some embodiments for a cartomizer such as shown in FIGS. 1-4.

FIG. 5 shows the cartomizer 200 and a case 500 for the cartomizer 200. The case comprises two components, a top housing 520 and a bottom housing 540 (adopting the same orientation as above for the cartomizer 200, whereby the mouthpiece 250 is located at the top of the cartomizer 200). The top housing 520 and the bottom housing 540 join together to provide an overall housing or case 500 for the cartomizer 200, and separate from one another to allow the cartomizer 200 to be inserted into, or removed from, the case 500. The case 500 is intended to hold a single cartomizer by itself (i.e. detached from an e-cigarette) in a sealed and secure environment.

The case 500 may be used to hold the cartomizer 200 prior to use by a consumer—e.g. for distribution through a retail supply chain, mail order delivery, etc. The case 500 may also be used by a consumer to hold the cartomizer 200 when removed from the control unit 300. For example, cartomizers may be supplied with different flavors of e-liquid, and a user may wish to swap between such cartomizers without necessarily first exhausting one of the cartomizers of e-liquid. Accordingly case 500 used to store a cartomizer 200 which is partly used, but which is not currently being used (and so is detached from control unit 300).

The case 500 may therefore be provided with the cartomizer 200 when initially purchased—e.g. the cartomizer 200 might be initially received by a consumer in the case 500. However, another possibility is that the case 500 may be separately acquired by the user, e.g. as a standalone item, for use with a cartomizer 200 that has been acquired separately from the case 500.

As can be seen from FIG. 5, the case 500 has a shape and dimensions that correspond generally to those of the cartomizer 200 (but slightly larger than the cartomizer 200, so that the cartomizer 200 can be accommodated in the case). Accordingly, the case 500 can retain a single cartomizer 200 (when detached from the control unit 200 or other component of the e-cigarette 100). Having the case fit snugly around the cartomizer 200 allows the case 500 to be generally as small as the cartomizer 200 permits—e.g. to make for ease of carrying, reduced material consumption, etc.

The case 500 is typically made of plastic material, such as polypropylene. The case 500 is generally rigid so as to provide some protection for the cartomizer 200 against mechanical damage (such as being dropped). However, the case 500 retains sufficient flexibility to allow for a resilient latching operation as described in more detail below. The case 500 is also substantially airtight (when closed)—protecting against the egress of e-liquid (and vapor from the e-liquid) from the cartomizer 200. Thus a low residual level of e-liquid vaporization occurs even if the cartomizer 200 is not activated, however, by retaining any such vapor in the case 500, this acts to suppress or inhibit further vaporization. The case 500 further protects against the ingress of substances that might damage the cartomizer 200 or contaminate the mouthpiece 250. More generally, the case 500 acts as a shield or cover to protect the mouthpiece 250 from contact with such potential contaminants.

Although FIG. 5 (and the other drawings) shows the case 500 as having smooth, opaque walls, in some embodiments, the case 500 may be transparent and/or have a textured surface. For example, a transparent (or partly transparent) housing may be provided to allow a user to see the cartomizer 200 inside the case 500—this may be helpful, e.g. if different flavor cartomizers are color-coded according to flavor. A textured (or partly textured) outer surface for the case 500 may be helpful for holding the case 500, especially for gripping the top and bottom housings to open the case 500 (as described in more detail below).

The case 500 primarily has gently curved, convex sides with rounded edges and corners. Since the case 500 will frequently be carried by a user, these curved sides and rounding of edges and corners helps to reduce the risk of the case 500 being snagged in clothing (or causing any fraying). The curved sides and rounded edges and corners also help to distribute stress more evenly, thereby making the case 500 more robust, and also supporting the operation of a latch as described in more detail below. The case 500 has two major faces which oppose one another, i.e. front and back, and hence has a generally planar structure. Having these two large faces supports a certain degree of flexing, which again support the operation of the latch as described below.

FIG. 6 provides further illustrations of the case 500, showing the case 500 with the top housing 520 engaged with the bottom housing 540. In particular, FIG. 6A is a front view of the case 500, using the same axes as shown in FIG. 1 for the e-cigarette 100. (Like the cartomizer 200, the case 500 is also front-back symmetric, so the allocation of front/back is arbitrary). FIG. 6B provides a side view of the cartomizer 200, again using the same axes as shown in FIG. 1. FIG. 6C shows a section through the case 500, and also through a cartomizer 200 contained therein, in respect of the plane denoted A-A in FIG. 6B.

FIG. 6 includes dimensions of the case 500, whereby it is indicated that the case 500 is 41.50 mm in width, 35.71 mm in height, and 21.00 mm in depth. The top housing 520 has a height of 23.46 mm while the bottom housing 540 has height of 15.25 mm. This implies 3.00 mm of overlap between the top housing 520 and the bottom housing 540 to provide a sealed enclosure within case 500. It will be appreciated that the dimensions shown in FIG. 6 are presented by way of example only, and other implementations may have different dimensions. Note however that the width of the case 500 is greater than the height of the case 500, and also significantly greater (by a factor of nearly 2, more generally, by a factor of at least 1.5) than the depth of the case 500.

The join between the top and bottom housings 520, 540 is formed at the point of greatest width of the cartomizer 200. This allows the case 500 to fit snugly around the cartomizer 200 as noted above, while still allowing the cartomizer 200 to be readily removed from the case 500 once opened (i.e. with the top housing 520 and the bottom housing 540 disengaged from one another).

As can be seen in FIG. 6C, the top housing 520 includes an inwardly directed protrusion or plug 524, approximately in the shape of a tapered cylinder, while the bottom housing 540 likewise includes an inwardly directed protrusion or plug 544, again approximately in the shape of a tapered cylinder. Both protrusions are located along the path of the central airflow through the cartomizer, and extend in towards the center of the case 500 (i.e. downwards for protrusion 524, upwards for protrusion 544).

Protrusion 524 is shown fitting into hole 280 of the mouthpiece 250 (see FIG. 3), while protrusion 544 fits into hole 214 on the underside of the base portion 210 of the cartomizer 200 (see FIG. 2). In this configuration, the protrusions 524, 544 not only retain the cartomizer 200 in position within the case 500, but also help to prevent leakage or other loss of e-liquid from the cartomizer 200. For example, by preventing airflow along the central air passage (from hole 214 to hole 280), this helps to minimize residual (room temperature) vaporization of the e-liquid. In addition, if any e-liquid escapes from the cartomizer 200, this is likewise held within the case 500 (rather than spilling out).

FIG. 7 provides further illustrations of the case 500. In particular, FIG. 7A is a view of the bottom housing 540 of the case, while FIG. 7B is a view of the top housing 520 of the case 500 (depicted bottom up to show certain internal details). FIG. 7C shows a section through the case 500, and also through a cartomizer 200 contained therein, in respect of a plane which is perpendicular to the plane denoted A-A in FIG. 6B (i.e. FIG. 7C shows the Z-Y plane using the orientation shown in FIG. 1).

As shown in FIG. 7A, the rim of the bottom housing 540 comprises a stepped arrangement. In particular, if we consider the housing wall to comprise an inner portion and an outer portion, then the inner portion extends higher than outer portion. This forms at the rim a ledge 547 where the outer portion of the wall terminates, and a raised portion 546, where the inner portion of the wall extends beyond the ledge 547 to form a step or raised portion 546. The front of the raised portion 546 is provided with an outwardly directed ridge 548 on its outside face (i.e. the ridge is raised in the Y direction away from the center of the device). This ridge generally extends in the X direction around the front of the rim. There is a corresponding ridge on the rear face of the bottom housing 540 (not visible in FIG. 7A, but as mentioned above, the case 500 is front/back symmetric).

Also visible in FIG. 7A is guide 551, which is also visible (more clearly) in FIG. 7C. The guide 551 is generally U-shaped (but with the bottom corners squared off, as shown in FIG. 7C). The base of the U is attached to the floor of the bottom housing 540, and is aligned with the front-back (Z) direction of the case 500. The two arms of the guide 551 extend upwards (approximately on either side of the central air passage through the cartomizer). The top of each arm of the guide is tapered, with a face 552A, 552B that slopes inwards towards the center of the case. When the cartomizer 200 is inserted into the bottom housing 540, the base portion 210 of the cartomizer 200 may first make contact with the guide 551. The tapered surfaces 552A, 552B of the guide 551 then direct the cartomizer 200 into a central position (in the Z-direction) with respect to the case 500, and thereby help to ensure that the plug 544 is properly received into hole 214 on the underside of the cartomizer 200.

As shown in FIG. 7B, the rim of top housing 520 also comprises a stepped arrangement. Again, if we consider the housing wall to comprise an inner portion and an outer portion, then the outer portion extends higher than inner portion (the opposite configuration to that shown in FIG. 7A for the bottom housing 540). This forms at the rim a ledge 527 where the inner portion of the wall terminates, and a raised portion 526, where the outer portion of the wall extends beyond the ledge 527 to form a step or raised portion 526. The front of the raised portion 526 is provided with an outwardly directed groove 528 on its inside face (i.e. sunk in the Y direction away from the center of the device). This groove generally extends in the X direction around the front of the rim. There is a corresponding groove on the rear face of the top housing 520 (not visible in FIG. 7B, but as mentioned above, the case 500 is front/back symmetric).

Each inside face of the top housing 520 includes a pair of inwardly directed fins 531A, 531B. Only the fins on one face are visible in FIG. 7B but there is a corresponding pair of fins on the opposing face; this symmetric configuration is visible in FIG. 7C. The fins 531 have an inner edge (i.e. furthest to their point of attachment to the housing) which slopes inwards towards the top of the case 500, such as shown in FIG. 7C. Accordingly, these fins 531 also act as a guide, in a similar manner to guide 551 in the bottom housing 540. In particular, when a cartomizer 200 is inserted into the top housing 520, the mouthpiece 250 may first make contact with the inner edge of the fins, which then guide the mouthpiece 250 into a central position (in the Z-direction) with respect to the case 500, and thereby help to ensure that the plug 524 is properly received into hole 280 on the top of the mouthpiece 250.

FIG. 7C shows how, when the case 500 is shut, the raised portion 526 of the top housing overlaps and fits outside the raised portion 546 of the bottom housing. In particular, the raised portion 526 of the top housing abuts the ledge 547 of the bottom housing 540. This overlap acts to form the closed, sealed environment within the case 500 when the top housing 520 is engaged with the bottom housing 540.

Furthermore, FIG. 7C shows that the case 500 includes a latch mechanism to hold the case securely in the closed position, with the top housing 520 engaged with the bottom housing 540. In particular, the ridge 548 on the outside of the raised portion 546 of the rim of the bottom housing 540 sits inside the corresponding groove 528 formed on the inside of the raised portion 526 of the rim of the top housing 520. Therefore, ridge 548 and groove 528 form a latch mechanism, in that the top housing 520 cannot be readily removed from the bottom housing 540 because the ridge 548 is, in effect, locked into the groove 528. In other words, in the configuration shown in FIG. 7C, the bottom side of the groove 528 abuts against the underside of the ridge 548, and so prevents the top housing 520 being removed directly from the bottom housing 540. Accordingly, this latch mechanism retains the cartomizer securely within the sealed environment of the case 500.

As noted above, the case 500 is generally rigid, but includes sufficient flexibility and resilience to accommodate the operation of the latch mechanism. In particular, the case 500 is sufficiently flexible to allow the front and back faces to deform resiliently to allow the ridge and groove to engage and disengage (this implies an ability for the faces to flex a distance corresponding approximately to the height/depth of the ridge and groove).

The engagement of the latch is supported by the top of the ridge 548 having a surface 549 which slopes in a downward, outward direction. Accordingly, when the case 500 is being shut, whereby the top housing and the bottom housing are being pushed together, the rim of the raised portion 526 of the top housing encounters this sloping surface 549 of the ridge. The sloping surface therefore converts the closing force (in the Y direction) into a displacing force in the Z direction, in particular, urging the raised portion 526 on the front/back faces of the top housing outwards, and conversely urging the raised portion 546 on the front/back faces of the bottom housing 540 inwards. This outward displacement of the top housing and inward displacement of the bottom housing allows the ridge 548 to pass along the inside of the raised portion 526 of the top housing until the ridge 548 encounters the groove 528. At this point, the resilience of the inwardly deformed bottom housing 540 and the outwardly deformed top housing 520 urge the ridge 548 and the groove 528 together, so that the ridge 548 is pushed inside the groove 528. In this configuration, the top housing 520 and bottom housing 540 are held latched together.

Figure 8B:
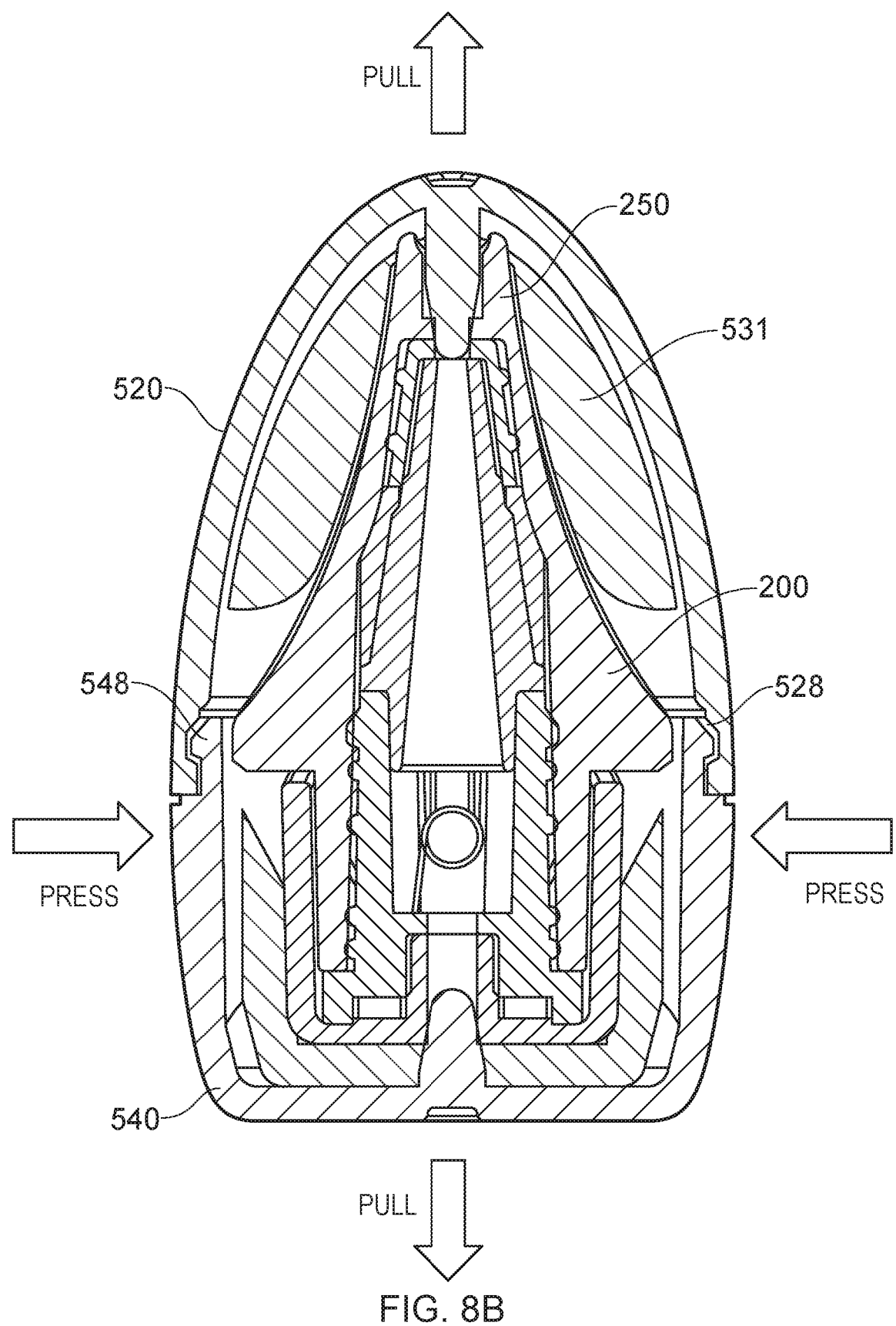
FIG. 8B is a section through the case and cartomizer therein corresponding to the section of FIG. 7C, but additionally illustrating a method of opening the case.

The case 500 supports two main methods for disengaging the latch mechanism to allow the case 500 to be opened by separating the top housing 520 and the bottom housing 540. A first, primary method is illustrated in FIG. 8A, which represents a section through the case 500 and cartomizer 200 therein, analogous to that of FIG. 6C. A second, secondary method is illustrated in FIG. 8B, which represents a section through the case and cartomizer therein, analogous to that of FIG. 7C.

In the method shown in FIG. 8A, the latch mechanism is released by pushing in simultaneously on the opposing sides of the top housing 520 of the case 500 (as indicated by the two "Press" arrows). Note that as the sides of the case 500 are pressed together in the method of FIG. 8A, this pushes together the overlapping raised portion 526 of the top housing 520 and raised portion 546 of the lower housing 540. However, the latch mechanism formed by ridges 548 and grooves 528 is located only on the front and back faces, rather than on the sides, so these sides surfaces can still directly slide over one another (albeit with slightly increased friction) in order to separate the top housing 520 from the bottom housing 540.

In contrast, the ridge 548 and groove 528 are located only on the front and back faces of the case 500 (but not the sides). This location of the ridges and grooves on the front/back faces arises because these surfaces are larger than the sides, and so have more scope to flex to engage (or disengage) the latch. Moreover, the front/back faces can accommodate longer grooves/ridges than the sides, and so can provide longer, and hence more secure, engagement for the latch mechanism.

One the latch is engaged, and the ridges and grooves are interlocked (as shown in FIG. 7C), the latch mechanism must be overcome to open the case 500. Pushing inwards the sides of the top housing 520, such as shown in FIG. 8A, does indeed unlatch the case 500, because this tends to deform (resiliently) the shape of the top housing 520, such that the front and back faces of the top housing 520 separate slightly from one another. This increased separation of the front and back faces of the top housing 520 displaces the grooves 528 outwards as well, in effect lifting them away front and back from the corresponding ridges 548. In other words, the ridges 548 on the front and back faces are no longer latched into the grooves 528, thereby allowing the top housing 520 to be separated from bottom housing 540. Once the case 500 has been opened, and the pressure released on the sides of the top housing 520, the top housing 520 will return to its original (undeformed) size and shape, Note that opening the case 500 in this manner to access the cartomizer 200 is a relatively complex operation—one hand is used to hold the top housing 520 on its sides, and then to compress the top housing 520 as shown in FIG. 8A, while a second hand is used to hold the bottom housing 540, thereby allowing the top housing 520 and bottom housing 540 to be pulled away from one another in order to open the case 500. However, the pressing on the sides and the pulling to open the case 500, such as shown in FIG. 8A, must be performed simultaneously. Otherwise, if the pressure on the sides is released before the top housing 520 and the bottom housing 540 are separated from one another, the top housing 520 returns to its original (undeformed) shape, whereby the latching mechanism of the ridges 548 and grooves 528 re-engages, hence latching the case 500 back in the closed position. It will be appreciated that this relatively complex opening operation, involving the use of both hands, helps to provide some protection against unintended or undesired opening of the case 500 (e.g. by small children).

In the method shown in FIG. 8B, the latch mechanism is released by pushing in simultaneously on the opposing faces of the bottom housing 540 of the case (as indicated by the two "Press" arrows). This cause the front and back faces of the bottom housing 540 to deflect inwards (resiliently), which in turn causes the front and back ridges 548 to withdraw from their respective grooves 528. This therefore releases the latch mechanism, thereby allowing the top housing 520 to be separated from the bottom housing 540 by pulling in the directions indicated in FIG. 8B in order to open the case 500.

Again, opening the case 500 in the manner shown in FIG. 8B to access the cartomizer 200 is a relatively complex operation—one hand is used to hold the front and back faces of the bottom housing 540 on its sides, and then to press them inwards, while a second hand is used to hold the top housing 520, thereby allowing the top housing 520 and bottom housing 540 to be pulled away from one another in order to open the case 500. However, as for the method of FIG. 8A, the pressing on the front and back faces and the pulling to open the case 500, such as shown in FIG. 8B, must be performed simultaneously. Otherwise, if the pressure on the front and back faces is released before the top housing 520 and the bottom housing 540 are separated from one another, the bottom housing 540 returns to its original (undeformed) shape, whereby the latching mechanism of the ridges 548 and grooves 528 re-engages, hence latching the case 500 back in the closed position. Again, it will be appreciated that this relatively complex opening operation, involving the use of both hands, helps to provide some protection against unintended or undesired opening of the case 500 (e.g. by small children).

One potential issue with opening the case 500 to access the cartomizer 200 is that the cartomizer 200 might fall directly out, e.g. to the floor, which is especially undesirable for a device that is to be used orally. This problem is particularly relevant for a case 500 such as described above, in which both hands are used simultaneously to open the case 500 (so that neither hand is available to hold the cartomizer 200 as the case is opened).

In order to address this issue, the fins 531 are used to grip the cartomizer 200 by the mouthpiece 250. In other words, the spacing between the opposing fins on the front and back faces of the top housing is slightly less than the depth (from front to back) of the mouthpiece 250. Accordingly, when the cartomizer 200 is inserted into the top housing 520, there is a slight interference fit between fins 531 and the mouthpiece 250, whereby the fins and/or mouthpiece deform slightly (and resiliently) in order to allow the mouthpiece 250 to be fully inserted into the top housing 520. Subsequently, when the case 500 is opened, the mouthpiece 250, and hence the cartomizer 200 as a whole, is retained in position in the top housing 520 (i.e. in the position shown in FIG. 8B) even when the bottom housing 540 of the case is removed. Thus the interference fit is tight or strong enough to withstand the (relatively small) weight of the cartomizer 200, thereby prevent the cartomizer 200 from falling out of the opened case 500. Rather the cartomizer 200 remains attached to the top housing 520, which is already being held by a user in order to open the case 500. This allows the user to put down the bottom housing 540, thereby freeing a hand to then specifically pull the cartomizer 200 out of the top housing 520 (without the risk of the cartomizer 200 accidentally falling out).

It will be appreciated that although various functionality has been described above in relation to certain particular implementations of a case 500 and cartomizer 200, analogous functionality can be provided in different implementations. For example, other embodiments of the case 500 may have a hinged lid (which might still be latched), a sliding door to open, etc. Furthermore various other forms of latching mechanism may be employed, rather than the interlocking ridge and groove described herein. Similarly, the facility to retain the cartomizer 200 in a portion of the case 500 even after opening of the case 500 may be implemented in many other forms of case 500 or for other forms of cartomizer 200.

Furthermore, although various embodiments and implementations have been described in detail herein, this is by way of example only, and it will be appreciated that a case such as described herein could be utilized with other forms of vapor provision system, for example, one that includes material derived from tobacco plants which is provided in any suitable form (powder, paste, shredded leaf material, etc, i.e. not liquid), and then heated to produce volatiles for inhalation by a user. More generally, the case may be used to store any cartridge that contains a consumable vapor precursor (e.g. e-liquid) for an e-cigarette or similar device. In some implementations, the cartridge may incorporate an atomizer or vaporizer (such a cartridge is often described as a cartomizer). The case may also be used with electronic vapor provision systems that have different types of heater for the e-cigarette, various types of airflow configuration, various types of connection between the cartomizer and the control unit (such as screw or bayonet) etc. The skilled person will be aware of further forms of electronic vapor provision system which might utilize such a case as described herein.

In conclusion, in order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. A case configured to receive a cartridge comprising a cartomizer, the cartomizer comprising a heating coil and an e-liquid, the cartridge contained and enclosed within the case, the case being adapted to hold a single cartridge by itself, detached from a vapor provision device, wherein the case comprises:

a substantially rigid housing that fits around the cartridge when detached from the electronic vapor provision device, the housing when closed providing a sealed environment for the cartridge, wherein the housing comprises at least one fin or protrusion that extends inward and is configured to contact the cartridge when the case is closed to provide a snug fit around the cartridge, wherein the case has a width direction which represents the largest dimension (DI) of the case and extends from side to side of the case, and wherein a first edge of the case which extends from side to side of the case is curved, and a second edge of the case, opposite to the first edge, extends from side to side of the case is substantially straight.

2. The case of claim 1, wherein the sealed environment acts to prevent egress of vapor from the cartridge and to prevent ingress of potential contaminants.

3. The case of claim 1, wherein the housing comprises a first housing portion and a second housing portion that separate to allow access to the cartridge.

4. The case of claim 1, wherein the case further includes an interlocking latch mechanism to hold the case in a closed position.

5. The case of claim 4, wherein at least a portion of the housing is configured to resiliently deform to disengage the interlocking latch mechanism.

6. The case of claim 1, wherein the case is formed of molded plastic.

7. The case of claim 6, wherein the case is formed of polypropylene.

8. The case of claim 1, wherein the case comprises two opposing major surfaces which are curved.

9. The case of claim 1, wherein all edges and corners of the case are curved or rounded.

10. The case of claim 1, wherein the case is symmetric with respect to a plane that is normal to the width direction.

11. The case of claim 1, wherein the case has a height direction which extends from the first edge to the second edge and which represents the second largest dimension (D2) of the case.

12. The case of claim 11, wherein the case is substantially planar in shape, lying in a plane corresponding to the height direction and the width direction.

13. The case of claim 11, wherein the case has a depth direction orthogonal to the height direction and the width direction and which represents the smallest dimension (D3) of the case, wherein $(D2*D2)/(D1*D3)>1$.